(12) United States Patent
Call et al.

(10) Patent No.: US 11,016,191 B2
(45) Date of Patent: *May 25, 2021

(54) NETWORK-BASED ULTRASOUND IMAGING SYSTEM

(71) Applicant: MAUI IMAGING, INC., San Jose, CA (US)

(72) Inventors: Josef R. Call, Campbell, CA (US); Henry A. Davis, Ash Fork, AZ (US); David M. Smith, Lodi, CA (US); David J. Specht, San Jose, CA (US); Viet Nam Le, San Jose, CA (US); Lang J. McHardy, San Jose, CA (US); Joseph James Digiovanni, II, Los Altos Hills, CA (US); Nathan W. Osborn, Palo Alto, CA (US); Bruce R. Ritzi, Sunnyvale, CA (US)

(73) Assignee: MAUI IMAGING, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/559,017

(22) Filed: Sep. 3, 2019

(65) Prior Publication Data

US 2020/0003896 A1 Jan. 2, 2020

Related U.S. Application Data

(63) Continuation of application No. 15/500,933, filed as application No. PCT/US2015/045703 on Aug. 18, 2015, now Pat. No. 10,401,493.

(Continued)

(51) Int. Cl.
*A61B 8/14* (2006.01)
*G01S 15/89* (2006.01)
(Continued)

(52) U.S. Cl.
CPC ............ *G01S 15/8929* (2013.01); *A61B 8/14* (2013.01); *A61B 8/483* (2013.01); *A61B 8/523* (2013.01);
(Continued)

(58) Field of Classification Search
None
See application file for complete search history.

(56) References Cited

U.S. PATENT DOCUMENTS 5,477,858 A * 12/1995 Norris ................. G01S 7/52033
600/441
6,565,510 B1 * 5/2003 Haider ................ A61B 5/0002
600/437

(Continued)

*Primary Examiner* — Chikaodili E Anyikire
(74) *Attorney, Agent, or Firm* — Shay Glenn LLP

(57) ABSTRACT

Systems and methods for network-based ultrasound imaging are provided, which can include a number of features. In some embodiments, an ultrasound imaging system images an object with three-dimensional unfocused pings and obtains digital sample sets from a plurality of receiver elements. A sub-set of the digital sample sets can be electronically transferred to a remote server, where the sub-set can be beamformed to produce a series of two-dimensional image frames. A video stream made up of the series of two-dimensional images frames can then be transferred from the remote server to a display device.

4 Claims, 9 Drawing Sheets

Related U.S. Application Data

(60) Provisional application No. 62/038,602, filed on Aug. 18, 2014.

(51) Int. Cl.
*A61B 8/08* (2006.01)
*A61B 8/00* (2006.01)
*G01S 7/52* (2006.01)
*G06F 3/14* (2006.01)

(52) U.S. Cl.
CPC ............ *A61B 8/5207* (2013.01); *A61B 8/565* (2013.01); *G01S 7/52053* (2013.01); *G01S 15/89* (2013.01); *G01S 15/8925* (2013.01); *G01S 15/8993* (2013.01); *G06F 3/14* (2013.01)

(56) References Cited

U.S. PATENT DOCUMENTS

| | | | |
|---|---|---|---|
| 2004/0015079 A1* | 1/2004 | Berger | A61B 18/02 600/437 |
| 2007/0161904 A1* | 7/2007 | Urbano | A61B 8/565 600/459 |
| 2008/0114250 A1* | 5/2008 | Urbano | A61B 8/4472 600/447 |
| 2008/0262357 A1* | 10/2008 | Wodnicki | G01S 7/52017 600/459 |
| 2011/0178441 A1* | 7/2011 | Tyler | A61N 5/0622 601/2 |
| 2012/0071710 A1* | 3/2012 | Gazdzinski | A61B 1/0002 600/101 |
| 2013/0144166 A1* | 6/2013 | Specht | A61B 8/4444 600/441 |
| 2013/0172743 A1* | 7/2013 | Brewer | A61B 8/466 600/440 |
| 2014/0056099 A1* | 2/2014 | Hancock | A61B 8/445 367/11 |
| 2017/0219704 A1* | 8/2017 | Call | A61B 8/14 |
| 2017/0363725 A1* | 12/2017 | Ignjatovic | G01S 15/8915 |

* cited by examiner

NETWORK-BASED ULTRASOUND IMAGING SYSTEM

CROSS-REFERENCE TO RELATED APPLICATIONS

This application is a continuation of U.S. application Ser. No. 15/500,933, filed Feb. 1, 2017, now U.S. Pat. No. 10,401,493, which application is the national stage under 35 USC 371 of International Application No. PCT/US2015/045703, filed Aug. 18, 2015, which application claims the benefit of U.S. Provisional Patent Application No. 62/038,602, filed Aug. 18, 2014, titled "Network-Based Ultrasound Imaging System", the contents of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates generally to the field of ultrasound imaging, and more particularly to a network-based ultrasound imaging system.

BACKGROUND

Ultrasound imaging provides for relatively low cost medical and non-medical imaging without the risks associated with ionizing radiation, or the complications of MRI imaging. Improvements to ultrasound imaging techniques combined with improvements to client-server networking architecture may provide additional opportunities for the use of ultrasound imaging to solve imaging challenges.

SUMMARY OF THE DISCLOSURE

A method of ultrasound imaging is provided, comprising transmitting an unfocused three-dimensional ping into an object from a transmitter element of a transducer array in a probe of a data capture device, receiving echoes of the unfocused three-dimensional ping with a plurality of receiver elements of the transducer array, converting analog signals from each of the plurality of receiver elements into a full dataset of digital sample sets, wherein the full dataset comprises digital sample sets from all the receiver elements, electronically transferring a sub-set of the digital sample sets to a remote server, wherein the sub-set comprises fewer digital samples than the full dataset, beamforming the sub-set of digital samples in the remote server to produce a series of two-dimensional image frames, and transferring a video stream made up of the series of two-dimensional image frames from the remote server to a display device.

In some embodiments, the method further comprises, in response to a control signal, transferring the full dataset from the data capture device to the remote server and storing the full dataset at the remote server.

In another embodiment, the method further comprises determining digital samples to include in the sub-set of digital samples by identifying digital samples associated with a selected imaging window from among the full dataset of digital sample sets.

In some embodiments, the display device is physically attached to the data capture device. In other embodiments, the display device is not physically attached to the data capture device. In further embodiments, the display device is a mobile device.

In some embodiments, the method further comprises selecting digital samples to include in the sub-set of digital samples by selecting only data samples corresponding to less than all pings transmitted from the probe.

In one embodiment, the method further comprises selecting digital samples to include in the sub-set of digital samples by selecting only data samples corresponding to less than all receive elements of the array.

In other embodiments, the method further comprises selecting digital samples to include in the sub-set of digital samples by selecting only data samples corresponding to less than all receive apertures of the array.

A network-based imaging system is provided, comprising a data capture device comprising a housing containing transmit control electronics configured to transmit ultrasound signals from a first plurality of transducer elements, receiver electronics configured to receive echoes of the transmitted ultrasound signals, the receiver electronics being further configured to digitize and store the received echoes as a full dataset in a first memory device physically located within a common housing of the data capture device, and communication electronics configured to communicate the full dataset. The system further comprises a remote server device comprising server communication electronics configured to receive the digitized echoes communicated by the communication electronics of the data capture device, beamforming software executed by the remote server device and configured to convert the received digitized echoes into a video stream of consecutive image frames, video streaming software executed by the remote server device and configured to stream the video to a display device.

In some embodiments, the display device further comprises user interface software executed by the display device and configured to receive user inputs to control one or more beamforming or video streaming parameters, and further configured to transfer user inputs to the beamforming software at the remote server device, the user interface software further comprising a user input control configured to transfer the full dataset to the remote server, and video display software executed by the display device and configured to receive the video stream from the remote server device and to display the video stream.

In some embodiments, the system further comprises a plurality of data capture devices in communication with the remote server device.

A method of collecting volumetric data representing a target object is provided, the method comprising transmitting an unfocused three-dimensional ping into the target object from a transmitter element of a transducer array in a probe, receiving echoes of the unfocused three-dimensional ping with a plurality of receiver elements of the transducer array, converting analog signals from each of the plurality of receiver elements into a full dataset of digital sample sets, wherein the full dataset comprises digital sample sets from all the receiver elements, electronically transferring a sub-set of the digital sample sets to a remote server, wherein the sub-set comprises fewer digital samples than the full dataset, beamforming the sub-set of digital samples in the remote server to produce a series of two-dimensional image frames, transferring a video stream made up of the series of two-dimensional image frames from the remote server to a mobile display device.

In some embodiments, the method further comprises, in response to a control signal, transferring the full dataset to the remote server and storing the full dataset at the remote server.

A method of ultrasound imaging is also provided comprising transmitting a plurality of unfocused three-dimensional pings into a three-dimensional target volume from a plurality of transmitter elements of a transducer array in a probe, receiving echoes of the unfocused three-dimensional pings with a plurality of receiver elements of the transducer array, converting analog signals from each of the plurality of receiver elements into a full dataset of digital sample sets, wherein the full dataset comprises digital sample sets from all the receiver elements, selecting a two-dimensional plane intersecting the three-dimensional target volume, identifying three-dimensional voxels intersecting the selected two-dimensional plane, identifying a sub-set of data samples corresponding to the selected two-dimensional plane, communicating only the sub-set of data samples over a computer network to a remote server, receiving, from the remote server, a video stream of two-dimensional images representing the selected two-dimensional plane, and displaying the video stream on a display device adjacent to the probe.

In some embodiments, the method further comprises, in response to a user command, communicating the full dataset to a remote data storage device.

DETAILED DESCRIPTION

Introduction and Definitions

Figure 1:
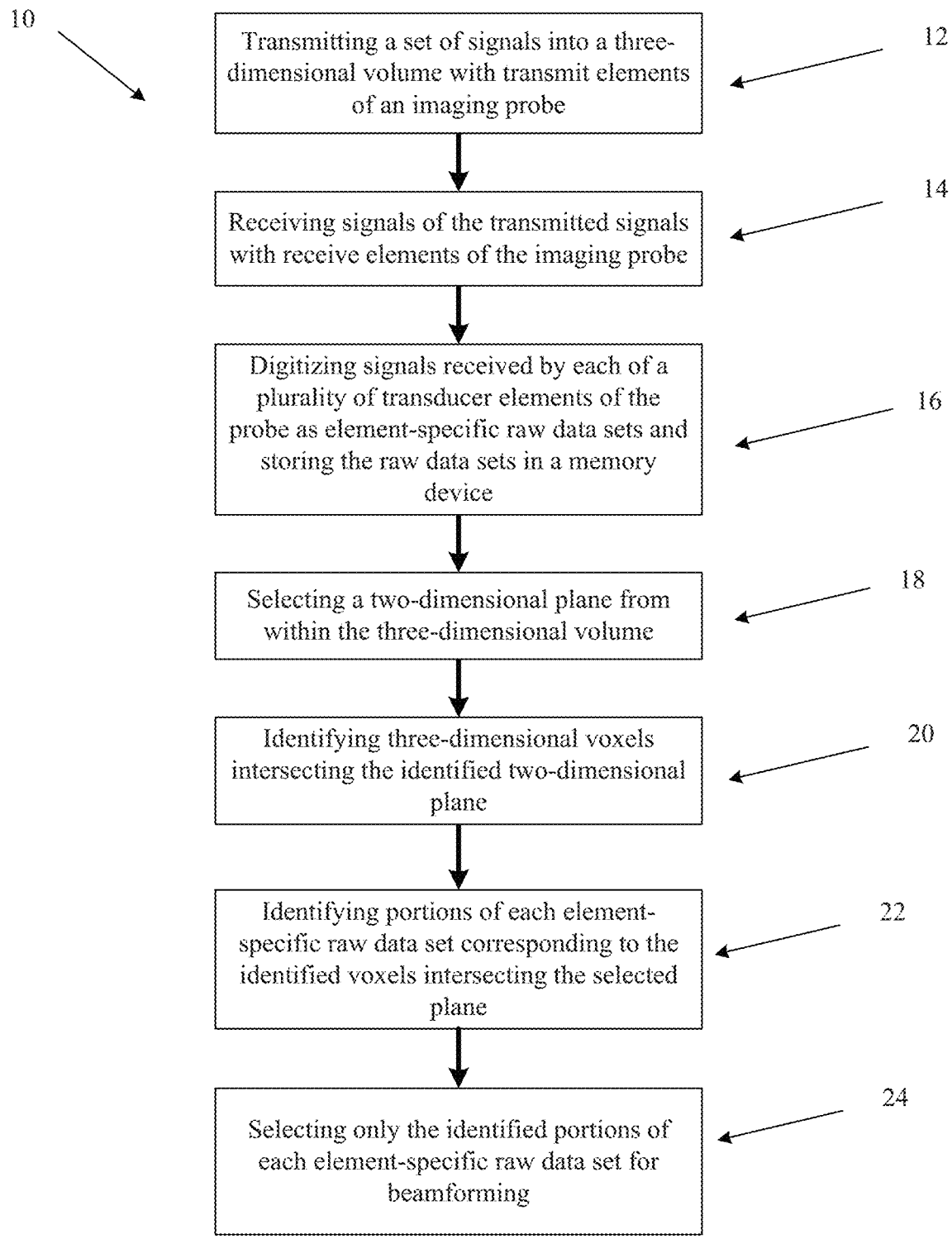
FIG. 1 is a process flow diagram illustrating an example process for directly beamforming a two-dimensional image plane from raw echo data obtained from a three-dimensional volume.

Although the various embodiments are described herein with reference to ultrasound imaging of various anatomic structures, it will be understood that many of the methods and devices shown and described herein may also be used in other applications, such as imaging and evaluating non-anatomic structures and objects. For example, the probes, systems and methods described herein may be used in non-destructive testing, inspection or evaluation of various mechanical objects, structural objects or materials, such as welds, pipes, beams, plates, pressure vessels, layered structures, etc. The various embodiments below include systems and methods for using an ultrasound imaging system that is configured to store raw, un-beamformed ultrasound data for subsequent beamforming and processing into image data. Such a system enables many unique methods of using ultrasound imaging systems.

Although examples are described herein with reference to transmission of ultrasound impulses into a medium to be imaged and reception of echoes of the transmitted ultrasound impulses. However, the skilled artisan will recognize that many of the techniques and systems described herein may be equally applicable to transmission and reception of other forms of energy, such as electromagnetic radiation including radio frequency signals, microwave signals, X-rays, or any other part of the electromagnetic spectrum.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In some other embodiments, ultrasound transducers may comprise capacitive micromachined ultrasound transducers (CMUT) or any other electro-acoustic transducer device. In some embodiments, transducers may comprise components for the transduction of other energy forms, such as electromagnetic radiation.

Transducers are often configured in arrays of multiple individual transducer elements. As used herein, the terms "transducer array" or "array" generally refers to a collection of transducer elements mounted to a common backing block. Such arrays may have one dimension (1D), two dimensions (2D), 1.X dimensions (1.XD) or three dimensions (3D). Other dimensioned arrays as understood by those skilled in the art may also be used. Annular arrays, such as concentric circular arrays and elliptical arrays may also be used. An element of a transducer array may be the smallest discretely functional component of an array. For example, in the case of an array of piezoelectric transducer elements, each element may be a single piezoelectric crystal or a single machined section of a piezoelectric crystal.

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Similarly, the term "receive element" may refer without limitation to an ultrasound transducer element which at least momentarily performs a receive function in which an ultrasound signal impinging on the element is converted into an electrical signal. Transmission of ultrasound into a medium may also be referred to herein as "insonifying." An object or structure which reflects ultrasound waves may be referred to as a "reflector" or a "scatterer."

As used herein, the term "aperture" may refer to a conceptual "opening" through which ultrasound signals may be sent and/or received. In actual practice, an aperture is simply a single transducer element or a group of transducer elements that are collectively managed as a common group by imaging control electronics or by beamforming electronics or software. For example, in some embodiments an aperture may be a physical grouping of elements which may be physically separated from elements of an adjacent aperture. However, adjacent apertures need not necessarily be physically separated.

It should be noted that the terms "receive aperture," "insonifying aperture," and/or "transmit aperture" are used herein to mean an individual element, a group of elements within an array, or even entire arrays within a common housing, or groups of elements in multiple separate arrays, that perform the desired transmit or receive function from a desired physical viewpoint or aperture. In some embodiments, such transmit and receive apertures may be created as physically separate components with dedicated functionality. In other embodiments, any number of send and/or receive apertures may be dynamically defined electronically as needed. In other embodiments, a multiple aperture ultrasound imaging system may use a combination of dedicated-function and dynamic-function apertures.

As used herein, the term "total aperture" refers to the total cumulative size of all imaging apertures. In other words, the term "total aperture" may refer to one or more dimensions defined by a maximum distance between the furthest-most transducer elements of any combination of send and/or receive elements used for a particular imaging cycle. Thus, the total aperture is made up of any number of sub-apertures designated as send or receive apertures for a particular cycle. In the case of a single-aperture imaging arrangement, the total aperture, sub-aperture, transmit aperture, and receive aperture will all have the same dimensions. In the case of a multiple array probe, the dimensions of the total aperture may include the sum of the dimensions of all of the arrays.

As used herein, the term "ping cycle" may refer to a cycle beginning with a ping signal being transmitted from a transmit aperture and echoes of that ping being received by receiver transducer elements. In some cases, echoes from two or more pings may be combined to form a single image frame, and multiple frames may be displayed in sequence to form a video. Thus, an "image cycle" may contain echoes from multiple ping cycles. In other cases, a single ping cycle may correspond to a single image cycle.

In some embodiments, two apertures may be located adjacent one another on a continuous array. In still other embodiments, two apertures may overlap one another on a continuous array, such that at least one element functions as part of two separate apertures. The location, function, number of elements and physical size of an aperture may be defined dynamically in any manner needed for a particular application. Constraints on these parameters for a particular application will be discussed below and/or will be clear to the skilled artisan.

Elements and arrays described herein may also be multi-function. That is, the designation of transducer elements or arrays as transmitters in one instance does not preclude their immediate redesignation as receivers in the next instance. Moreover, embodiments of the control system herein include the capabilities for making such designations electronically based on user inputs, pre-set scan or resolution criteria, or other automatically determined criteria.

As used herein the term "point source transmission" or "ping" may refer to an introduction of transmitted ultrasound energy into a medium from a single spatial location. This may be accomplished using a single ultrasound transducer element or combination of adjacent transducer elements transmitting together as a single transmit aperture. A single transmission from a point source transmit aperture approximates a uniform spherical wave front, or in the case of imaging a 2D slice, a uniform circular wave front within the 2D slice. In some cases, a single transmission of a circular or spherical wave front from a point source transmit aperture may be referred to herein as a "ping" or a "point source pulse."

As used herein, the phrase "pixel resolution" refers to a measure of a number of pixels in an image, and may be expressed with two positive integers, the first referring to a number of pixel columns (image width) and the second referring to a number of pixel rows (image height). Alternatively, pixel resolution may be expressed in terms of a total number of pixels (e.g., the product of the number of rows and the number of columns), a number of pixels per unit length, or a number of pixels per unit area. "Pixel resolution" as used herein is distinct from other uses of the term "resolution" which refers to the level of detail visible in an image. For example, "lateral resolution" may refer to the level of detail that may be discerned along a horizontal axis in an ultrasound image plane, independent of how an image of such a plane may be represented as a digital image made up of pixels.

Ping-Based Ultrasound Imaging

In various embodiments, point-source transmission ultrasound imaging, otherwise referred to as ping-based ultrasound imaging, provides several advantages over traditional scanline-based imaging. Point source transmission differs in its spatial characteristics from a "phased array transmission" which focuses energy in a particular direction from the transducer element array along a directed scanline. An unfocused point source pulse (ping) may be transmitted so as to insonify as wide an area as possible with an unfocused wavefront.

In some cases, an unfocused "circular" wavefront may be transmitted into a single image plane or "scanning plane." Such two-dimensional focusing may be achieved by providing a lensing material between a transducer element and an object to be imaged. A ping focused into a single plane may be referred to as a two-dimensional ping.

For volumetric imaging, an unfocused three-dimensional ping may be transmitted to form a substantially spherical wavefront which may be referred to as a three-dimensional ping.

Echoes of a transmitted ping will be returned from scatterers in the region of interest and may be received by all of the receiver elements of a probe. The receiver elements may be grouped into "receive apertures" as will be further described below. Those echo signals may be filtered, amplified, digitized and stored in short term or long term memory (depending on the needs or capabilities of a particular system).

Images may then be reconstructed from received echoes by assuming that the wavefronts emitted from the point source are physically circular (for 2D imaging) or spherical (for 3D imaging) in the region of interest. In actuality, a two-dimensionally focused wavefront may also have some penetration in the dimension normal to the 2D image plane. That is, some energy may essentially "leak" into the dimension perpendicular to the desired two-dimensional imaging plane.

Additionally, a "circular" wavefront may be limited to a semicircle or a fraction of a circle less than 180 degrees ahead of the front face of the transducer according to the unique off-axis properties of a transducing material. Similarly, when transmitting three-dimensional "spherical" pings, the corresponding wavefronts may have a shape of a semi-sphere or a smaller fractional sphere section (e.g., a "cone" shape), depending on the off-axis characteristics of the transmit element(s) used.

The process of forming an image from received echoes is generally referred to herein as "beamforming." In ping-based imaging, beamforming may generally involve determining an echo sample corresponding to each pixel or voxel position within an image window. Alternately, beamforming may involve the reverse, that is determining a pixel display location for each received echo sample. Because each ping insonifies an entire imaged region, a "complete" (albeit low quality) image may be formed with the echoes of a single transducer element. An image that may be formed from echoes received by a single receive transducer element may be referred to as a sub-image. The image quality may be improved by combining sub-images formed from echoes received at a plurality of transducer elements. Transducer elements may be grouped into "apertures," and sub-images from elements of a common aperture may be combined to form an image layer.

Beamforming of ping-based echoes may be performed using a software-based or hardware-based dynamic beamforming technique, in which a beamformer's focus may be continuously changed to focus at a particular pixel position as that pixel is being imaged. Such a beamformer may be used to plot the position of echoes received from a point source pulse. In some embodiments, a dynamic beamformer may plot the locus of each echo signal based on a round-trip travel time of the signal from the transmitter to an individual receive transducer element.

When beamforming echoes of a transmitted two-dimensionally focused ping, the locus of a single reflector will lie along an ellipse with a first elliptical focus at the position of the transmit transducer element(s) and the second elliptical focus at the position of the receive transducer element. Although several other possible reflectors lie along the same ellipse, echoes of the same reflector will also be received by each of the other receive transducer elements of a receive aperture. The slightly different positions of each receive transducer element means that each receive element will define a slightly different ellipse for a given reflector. Accumulating the results by coherently summing the ellipses for all elements of a common receive aperture will indicate an intersection of the ellipses for the reflector, thereby converging towards a point at which to display a pixel representing the reflector. The echo amplitudes received by any number of receive elements may thereby be combined into each pixel value. In other embodiments the computation can be organized differently to arrive at substantially the same image.

When beamforming echoes of a transmitted three-dimensional ping, substantially the same process may be followed, but the possible locus of each reflector lies on a three-dimensional ellipsoid with a first ellipsoidal focus at the position of the transmit transducer element, and a second ellipsoidal focus at the position of the receiving transducer element. Therefore, combining impressions of a particular reflector obtained with multiple receive elements may produce a voxel point at the three-dimensional intersection of the multiple ellipsoids.

Errors in information describing the relative three-dimensional position of transmitting and receiving elements may substantially degrade image quality. Therefore, a calibration process may be used to minimize error in element position information.

Various algorithms may be used for combining echo signals received by separate receive elements. For example, some embodiments may process echo signals individually, plotting each echo signal at all possible locations along its ellipse, then proceeding to the next echo signal. Alternatively, each pixel location may be processed individually, identifying and processing all echoes potentially contributing to that pixel location before proceeding to the next 2D pixel or 3D voxel location.

Image quality may be further improved by combining images formed by the beamformer from one or more subsequent transmitted pings, transmitted from the same or a different point source (or multiple different point sources). Improvements to image quality may be obtained by combining images formed by more than one receive aperture. The process of combining separately beamformed images, pixels or voxels may be referred to herein as "image layer combining." Combining images from echoes received at multiple, separate apertures of a multiple aperture ultrasound probe may further improve image quality. The term "image layer combining" may refer to the combination of two or more overlapping pixel values, voxel values, or complete images (i.e., arrays of pixel and/or voxel values), where the overlapping values are obtained using different transmitted pings, different transmit apertures, and/or different receive apertures. Examples of image layer combining processes are described in Applicant's prior applications referenced and incorporated by reference herein.

In some embodiments, ping-based multiple aperture imaging may operate by transmitting a point-source ping (e.g., a 2D ping or a 3D ping) from a first transmit aperture and receiving echoes with elements of two or more receive apertures, one or more of which may include some or all elements of a transmit aperture. An image may be formed by triangulating the position of scatterers based on delay times between ping transmission and reception of echoes, the speed of sound, and the relative positions of transmit and receive transducer elements. As a result, a sub-image of the entire insonified region may be formed from echoes of each transmitted ping received by each receive element. Coherently combining sub-images from echoes received by multiple elements grouped into a first receive aperture may produce the improvement described above with reference to intersecting ellipses. Sub-images from echoes received by multiple elements grouped into a second receive aperture may also be coherently combined with one another, and then the first-aperture image and the second-aperture image may be combined coherently or incoherently.

In some embodiments, a single time domain frame may be formed by combining images formed from echoes received at two or more receive apertures from a single transmitted ping. In other embodiments, a single time domain frame may be formed by combining images formed from echoes received at one or more receive apertures from two or more transmitted pings. In some such embodiments, the multiple transmitted pings may originate from different transmit apertures.

The same ping-based imaging techniques may be applied to 3D volumetric data by transmitting ping signals that are not constrained to a single plane (e.g., three-dimensional semi-spherical or near-semi-spherical ultrasound signals), and receiving echoes with receive elements displaced from one another in two dimensions perpendicular a line extending into the imaged medium, as described herein and in Applicant's previous applications. Multiple aperture ultrasound probes configured for ping-based 3D volumetric imaging may have large total apertures, which may be substantially greater than any expected coherence width for an intended imaging application. Examples of multiple aperture ultrasound probes are shown and described in Applicant's U.S. patent application Ser. No. 13/272,105, published as US 2012/0095343 (now U.S. Pat. No. 9,247,926), and U.S. patent application Ser. No. 14/279,052 (now U.S. Pat. No. 9,883,848), both of which are incorporated by reference herein.

3D volumetric data may be captured and stored using substantially the same systems and methods described above. Typically, a multiple aperture probe for 3D imaging may have substantially more transducer elements than a probe intended primarily for 2D imaging. As such, an imaging system for capturing and storing 3D volumetric data during a ping-based imaging process may include substantially more receive channels and may also include a larger capacity raw data memory device. The raw echo data obtained with a probe for 3D volumetric imaging may be stored in the memory device. Such volumetric raw data may be structured similarly to data captured with a probe configured for 2D imaging, such that echoes may be distinguished based on the particular receive element that received them and the particular transmitted ping that generated the echoes.

Beamforming 3D ping-based echo data may also be performed using similar systems and methods to those used for beamforming 2D ping-based echo data. Each digitized sample value may represent a scatterer from the insonified region of interest. As in the 2D case, the amplitude of each received sample along with its time of arrival and the exact three-dimensional positions of the transmitting and receiving transducers may be analyzed to define a locus of points identifying potential positions of the scatterer. In the 3D case, such a locus is a three-dimensional ellipsoid having as its foci the positions of the transmitting and receiving transducer elements. Each unique combination of transmitting and receiving transducer elements may define a separate view of the same reflector. Thus, by combining information from multiple transmit-receive transducer element combinations, the actual three-dimensional location of each reflector may be more accurately represented as a three-dimensional point or voxel in a three-dimensional volume.

For example, in some embodiments a 3D array of voxels representing reflectors in a 3D volume may be assembled in computer memory by beginning with an evaluation of a selected digital sample. The selected digitized sample value may be written into every voxel indicated by the corresponding ellipsoid as described above. Proceeding to do the same with every other collected sample value, and then combining all resulting ellipsoids may produce a more refined image. Real scatterers may be indicated by the intersection of many ellipsoids whereas parts of the ellipsoids not reinforced by other ellipsoids may have low levels of signal and may be eliminated or reduced by filters or other image processing steps.

In other embodiments, the order of computation may be changed by beginning with a selected voxel in a final 3D volume representation to be produced. For example, for a selected voxel, the closest stored sample may be identified for each transmitter/receiver pair. All samples corresponding to the selected voxel (i.e., all samples with an ellipsoid that intersects the voxel) may then be evaluated and summed (or averaged) to produce a final representation of the voxel. Closeness of a sample to a selected voxel may be determined by calculating the vector distance from the three-dimensional position of a transmitter (i.e., the transmitter from which the ping signal was transmitted to produce the echo sample) to the selected voxel position plus the vector distance from the selected voxel position to the position of a receiver at which the sample was received. Such a linear distance may be related to the time-divided sample values by dividing the total path length by speed of sound through the imaged object. If received data samples are stored and/or indexed based on the time after a transmitted ping at which they were received, then samples corresponding to a particular voxel may be identified based on the element position data and speed-of-sound data as described above. Using such methods, the samples corresponding to a calculated time may be associated with the selected voxel.

In some embodiments, a voxel of a final 3D volume representation may be made up of combined data from multiple receive elements, from multiple receive apertures, from multiple pings, or various combinations of these. An example will now be described with reference to an arbitrarily selected voxel. A first ping signal may be transmitted from a first transmit element, and the echoes received by each receive elements may be digitized and stored separately (e.g., one echo string per receive element per ping). A first set of echo data may be identified as representing energy from the first ping corresponding to the selected voxel received by elements of a first receive aperture. A second set of echo data generated from the first ping may also be identified as corresponding to the selected voxel received by elements of a second receive aperture.

A second ping signal may then be transmitted from a second, different transmit element. A third set of echo data representing energy from the second ping may be identified as corresponding to the selected voxel received by elements of the first receive aperture. A fourth set of echo data of the second ping may be identified as corresponding to the selected voxel received by elements of the second receive aperture.

As will be clear in view of the present disclosure, data received each element of the first receive aperture may provide a separate representation of each voxel in the imaged volume. Thus, the first data set may contain multiple data points representing the selected voxel as received by the individual elements of the first receive aperture. The data points of the first data set may be coherently combined with one another to produce a first impression of the selected voxel. The data points of the second data set representing signals from the first ping received by elements of the second receive aperture may be coherently combined with one another to produce a second impression of the selected voxel. The data points of the third data set representing signals from the second ping received by elements of the first receive aperture may be coherently combined with one another to produce a third impression of the example. The data points of the fourth data set representing signals from the second ping received by elements of the second receive aperture may be coherently combined with one another to produce a fourth impression of the selected voxel.

The first selected voxel impression may be coherently combined with the third selected voxel impression to form a first combined voxel impression of the selected voxel. Because both the first impression and the third impression were obtained with the same receive aperture, they may be combined coherently without risking phase cancellation (assuming the first receive aperture is sized to be less than a maximum coherent width for an intended imaging application).

The second impression of the selected voxel may be coherently combined with the fourth impression to form a second combined voxel impression of the selected voxel.

In some embodiments the step of coherently combining data from the first ping received by the elements of the first aperture with the data from the second ping received by the same elements of the same first receive aperture may be performed before any other combining steps. In some embodiments, combination of signals from two separate pings received by the same receive elements may be performed before or simultaneously with combining signals received by elements of a common receive aperture. In some embodiments, some coherent combinations of received signals may be performed electronically (i.e., by combining analog signals) before digitizing the received signals.

The first combined voxel impression may be combined with the second combined voxel impression. If the total aperture defined by the first receive aperture and the second receive aperture is greater than a total coherent width for the imaging application, then the first combined voxel impression may be combined incoherently with the second combined voxel impression to obtain a final representation of the selected voxel.

These steps of combining impressions of a selected voxel may be repeated or performed in parallel for each voxel of the imaged three-dimensional volume to obtain a final representation of the entire volume. In other embodiments, the steps may be performed in any other sequence, with any number of transmitted pings, and with any number of receive apertures. Various other combinations of coherent and incoherent summation techniques may also be used when combining signals from multiple receive elements, receive apertures, and/or pings.

In some embodiments, after the above example process or another process has been used to form a complete representation of the 3D volume, a single plane may be selected for display by identifying a collection of voxels making up the selected plane, and displaying the data from those voxel on a two-dimensional display.

In other embodiments, a selected two-dimensional plane may be beamformed directly from volumetric raw data instead of beamforming a complete 3D volume. This may be desirable in order to reduce a quantity of processing needed to produce an image of a selected plane.

FIG. 1 illustrates an example embodiment of a process 10 for beamforming a two-dimensional plane from three-dimensional data obtained by a ping-based multiple aperture imaging system. As shown at block 12, imaging signals may be transmitted into a three-dimensional volume. At block 14, signals from the transmitted signals may be received by receive elements of the imaging probe. Block 16 may comprise digitizing signals received by each receive transducer element of the probe as element-specific raw data sets (i.e., complete echo strings corresponding to each receive channel as described elsewhere herein). At block 18, a two-dimensional image plane within the insonified three-dimensional volume may be identified manually by a user or automatically by an imaging device or other system. At block 20, three-dimensional voxels intersecting the selected image plane may be identified. At block 22, the process may include identifying portions of each of the complete element-specific raw data sets corresponding to the identified voxels. The portions of the data sets may comprise complete samples and/or interpolated positions between samples. Identifying data samples corresponding to specified voxels may be performed based on known positions of transmit and receive elements and a speed-of-sound value (which may be based on an ultrasound frequency and the composition of an imaged medium) as described above. At block 24, the process may proceed by selecting only the identified samples for beamforming to determine display values for each pixel of the selected two-dimensional image plane.

Figure 2:
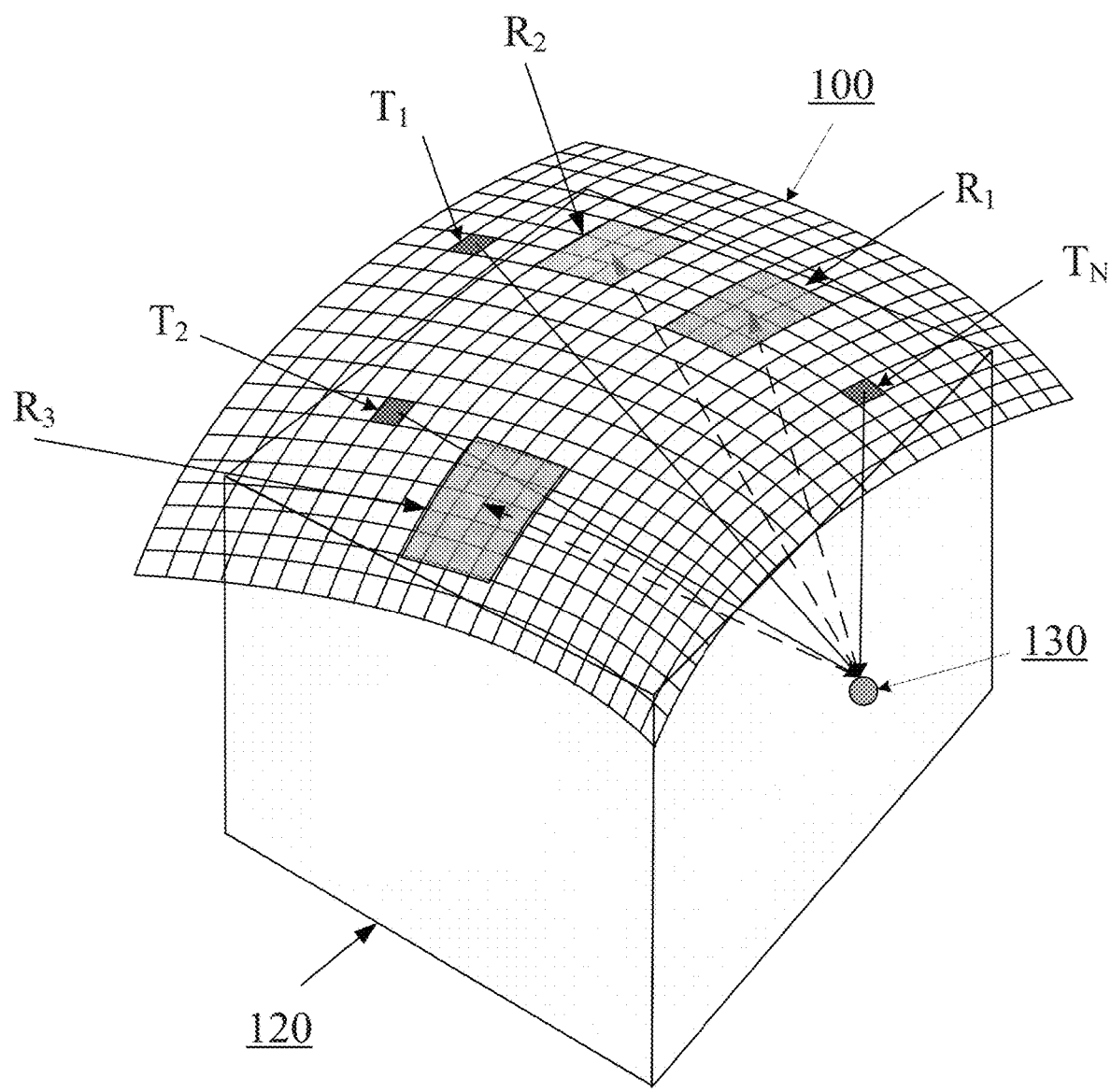
FIG. 2 is a schematic perspective illustration of a multiple aperture imaging system for imaging a three-dimensional volume.
Figure 3:
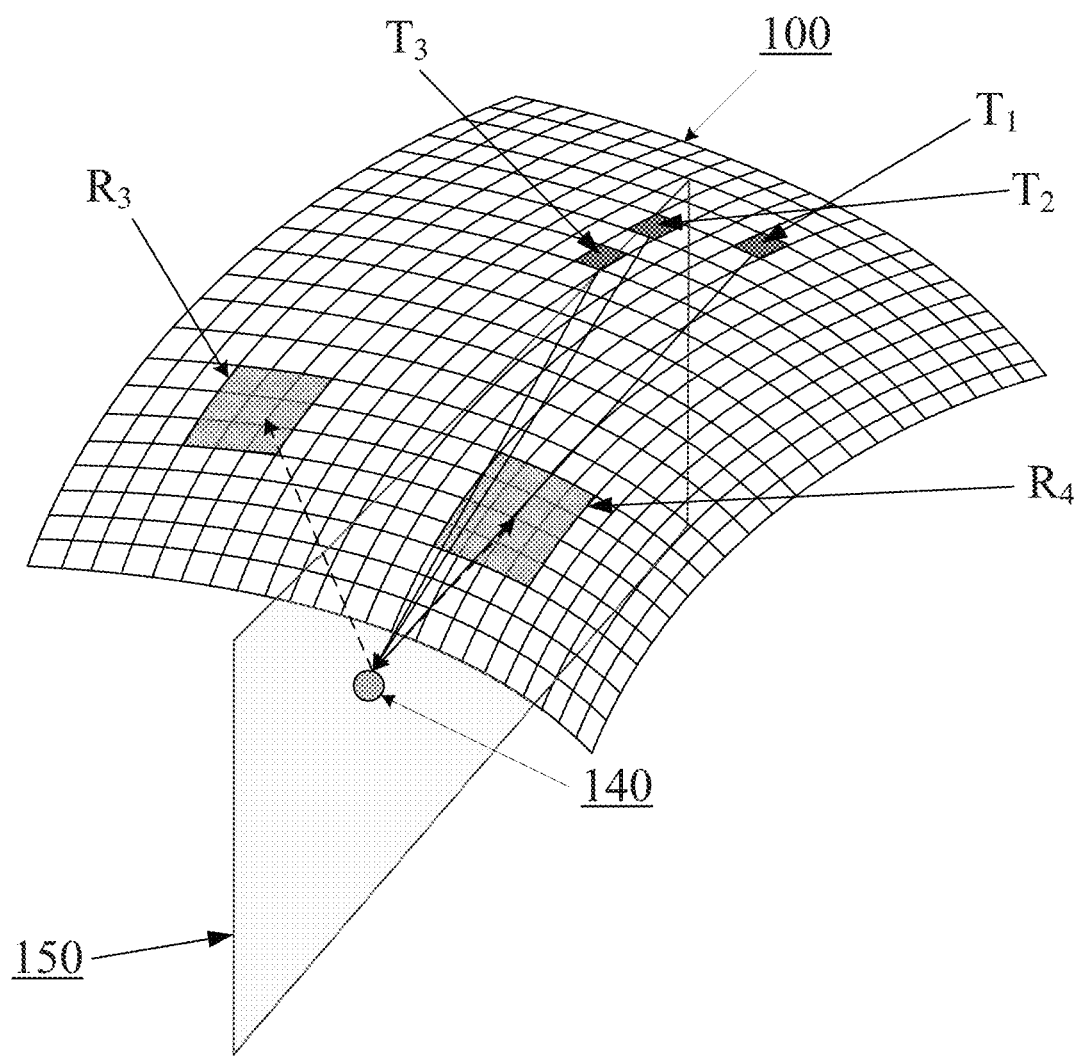
FIG. 3 is a schematic perspective illustration of a multiple aperture imaging system imaging a two-dimensional plane within a three-dimensional volume.

FIG. 2 illustrates a schematic representation of an example three-dimensional multiple aperture ultrasound imaging probe array 100 (probe housing and support structures are omitted from the drawing for simplicity) comprising an array of transducer elements and a region of interest 120 to be imaged represented as a rectangular block (an actual shape and size of an insonified region may depend on details of the probe being used). The probe arrays 100 of FIG. 2 and FIG. 3 are shown as having curvature about two orthogonal axes, thereby forming a three-dimensional array with all elements spaced from one another in at least two dimensions. In alternative embodiments, a probe array may be substantially flat with all elements lying in substantially the same two-dimensional plane. In further embodiments, any other configuration is also possible. For example, some elements may lie on a common plane while others may be angled inwards or outwards relative to an object to be imaged. As will be clear in view of the disclosure herein, as long as the position of each element is known to a desired degree of precision and accuracy, any array shape may be used, though some array configurations may be more optimally configured for a particular imaging application.

The probe array 100 is shown with a plurality of transmit elements $T_1$, $T_2$, and $T_n$ highlighted. In some cases transmit elements may be dedicated for transmit only, while in other cases, any of the transducer elements may be temporarily designated as a transmit element for a particular image cycle or ping cycle. In some embodiments, any element of the array may be temporarily or permanently designated and used as a transmit element. In other embodiments, transmit elements may be configured differently than receive elements and/or may be used exclusively for transmitting. Transmit elements may be located at any position within a two-dimensional or three-dimensional array.

In some embodiments, some or all elements of the array 10 may be configured to receive echoes of transmitted signals. Such receive elements may be grouped into a plurality of receive apertures, each receive aperture comprising one or more receive elements as described herein. Grouping of elements into receive apertures may be performed at any time before or after imaging is performed. Furthermore, using stored raw echo data, receive apertures may be re-defined after collecting echo data, as described in further detail below.

FIG. 2 shows two receive apertures $R_1$, $R_2$, and $R_3$. As shown, R1 is made up of more elements than R2. It should be understood that each of the receive apertures may include any number of transducer elements which may be spaced from one another in one, two or three dimensions. The elements of the probe array may be grouped into any number of receive apertures as needed. Because echoes of each ping may be received by all or substantially all of the receive elements, and raw echo data from echoes received by each element may be digitized and stored in a raw data memory, the grouping of receive elements into receive apertures may be established or adjusted prior to imaging, during live imaging, or during subsequent review of stored raw data in order to optimize the arrangement of apertures for a given imaging scenario.

In some embodiments, the size of a receive aperture may be limited by the assumption that the speed of sound is the same for every path from a scatterer to each element of the receive aperture. In a narrow enough receive aperture this simplifying assumption is acceptable. However, as receive aperture width increases, an inflection point is reached (referred to herein as the "maximum coherent aperture width," "maximum coherent width" or "coherence width") at which the echo return paths will necessarily pass though different types of tissue having different speeds of sound. When this aggregate difference results in phase shifts approaching 180 degrees, additional receive elements beyond the maximum coherent receive aperture width will tend to degrade the image rather than improve it.

Therefore, in order to make use of a wide probe with a total aperture width greater than the maximum coherent width, the full probe width may be physically or logically divided into multiple apertures, each of which may be limited to a maximum width (e.g., a circular diameter, an ellipse major axis length, or a rectangular/square aperture's diagonal length) no greater than the maximum coherent aperture width for an intended imaging application (that is, small enough to avoid phase cancellation of received signals). The maximum coherent width can be different for different patients and for different probe positions on the same patient. In some embodiments, a compromise width may be determined for a given imaging scenario. In other embodiments, a multiple aperture ultrasound imaging control system may be configured with a dynamic control mechanism to subdivide the available elements in multiple apertures into groups that are small enough to avoid destructive phase cancellation. Determining such a maximum aperture width may be achieved by sequentially evaluating images, image data, or other data produced using incrementally larger apertures until phase cancellation is detected, and then backing up by one or more aperture size increments.

In some embodiments, it may be more difficult to meet design constraints while grouping elements into apertures with a width less than the maximum coherent width. For example, if the material being examined is too heterogeneous over very small areas, it may be impractical or too costly to form apertures small enough to be less than the maximum coherent width. Similarly, if a system is designed to image a very small target at a substantial depth, an aperture with a width greater than the accepted maximum coherent width may be needed. In such cases, a receive aperture with a width greater than the maximum coherent width can be accommodated by making additional adjustments, or corrections may be made to account for differences in the speed-of-sound along different paths, allowing the region just enveloping the very small, very deep target to be brought into precise focus while other regions may be slightly defocused. Some examples of such speed-of-sound adjustments are provided here, while other methods may also be known.

Because ping signals insonify an entire region to be imaged, volumetric echo data obtained via three-dimensional ping-based imaging is seamless. By contrast, volumetric data assembled from a series of 2D planar slices tend to require some amount of interpolation of image data in the spaces between adjacent planar slices. Similarly, individual 2D images assembled from a series of scanlines typically require some amount of interpolation of image data in the spaces between adjacent scanlines.

The seamless nature of ping-based volumetric echo data means that any arbitrary 2D slices taken through any portion of a 3D volume may be beamformed and displayed without the need for interpolation. In some cases, non-planar or curved slices may also be taken through a section of volumetric data. The result of such a non-planar or curved-path slice may be displayed on a two-dimensional display, either as a flattened planar image or as a perspective rendering. Volumetric information may also be presented via a three-dimensional display such as a holographic display or a stereoscopic display. Therefore, in some embodiments, raw echo data from a volumetric imaging session may be retrieved from a memory device, some or all of the volume may be beamformed and displayed as an image, a desired region of the volume may be selected (automatically by software or manually by an operator), and the selected region may be re-beamformed and presented as a new image. Volumetric raw echo data may also be used in a wide range of other ways, as described below.

FIG. 3 illustrates a schematic probe array 100 highlighting a plurality of transmit elements T1, T2, T3, T4, T5, and two receive aperture groups of elements R3 and R4. FIG. 3 also shows ray lines indicating paths traveled by ultrasound energy transmitted by each transmit element T1, T2, T3, T4, T5, to a reflector 140 within a single 2D plane 150 and dashed ray lines representing the paths traveled by echoes reflected by the reflector 140 and received at each of the receive apertures R3 and R4. As can be seen, although the transmit elements and the receiver elements do not all lie along a common plane, reflectors lying within the indicated 2D plane 150 can be illuminated with ultrasound energy from any of the transmit elements, and echoes may be received by receive elements located anywhere in the probe array 100.

Thus, even using a volumetric probe, reflectors lying along a single two-dimensional plane (e.g., plane 150) may be selected for beamforming and display from within an insonified three-dimensional volume. The use of transmitters and receivers not on the image plane makes possible point spread functions that are much smaller in the dimension perpendicular to the image plane than point spread functions in the same plane obtained with a 2D probe (i.e., a probe configured to transmit and receive energy focused within the image plane).

As will be described in further detail below, beamforming of received echo data may be performed in real-time during a live imaging session, and/or at a later time by retrieving raw echo data of an imaging session. Depending on a probe used, and the needs of a particular application, raw echo data sets may be collected and stored for imaging sessions covering one or more individual two-dimensional planes, or for complete three-dimensional volumes.

Raw Echo Data

Figure 4:
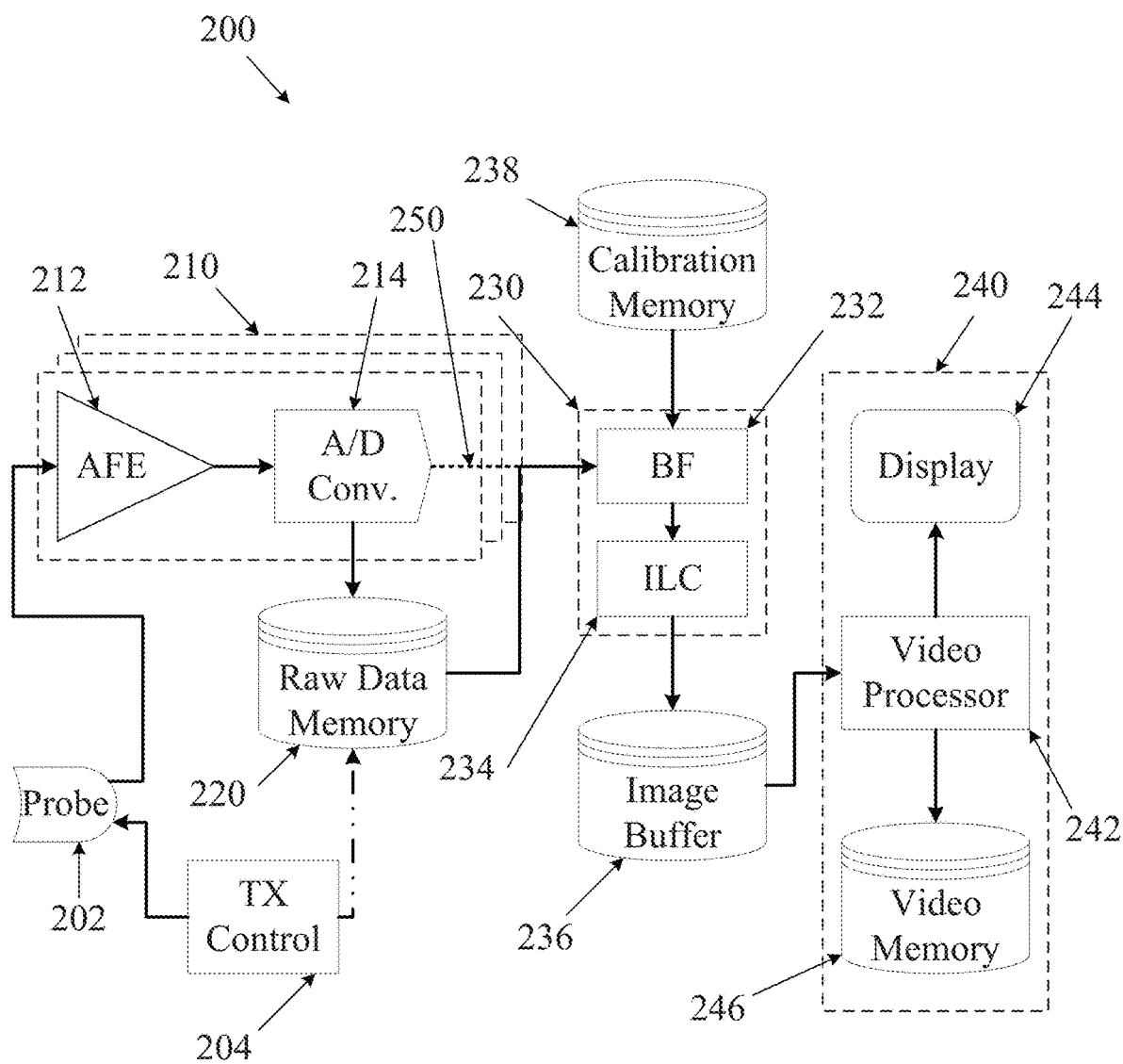
FIG. 4 is a schematic illustration of an embodiment of an imaging system incorporating a raw data memory.

FIG. 4 is a block diagram illustrating components that may be included in some embodiments of an ultrasound imaging system 200. The diagram of FIG. 4 includes several subsystems: a transmit control subsystem 204, a probe subsystem 202, a receive subsystem 210, an image generation subsystem 230, and a video subsystem 240. Unlike most ultrasound systems, the system of FIG. 4 provides a memory device configured to store raw, un-beamformed echo data for later retrieval and processing. In some embodiments, the various subsystems may be physically and logically contained within a single device. In other embodiments, some or all of the subsystems may be contained in physically separate devices or systems that may be in communication with other devices containing some or all of the other subsystems. Additional details of the elements of FIG. 4 are described in Applicant's U.S. patent application Ser. No. 13/971,689, published as US Publication No. 2014/0058266 (now U.S. Pat. No. 9,986,969), the entirety of which is incorporated by reference herein.

The transmit control subsystem may generally comprise control electronics for determining the shape, timing, frequency or other characteristics of transmitted ultrasound pulses. The probe subsystem may include any probe configured to transmit ultrasound energy into a medium to be imaged and to receive echoes of the transmitted energy from within the medium. In some cases, transmit and receive functions may be divided into physically, electronically, and/or logically separate devices, and in some cases, a receive probe may receive directly-transmitted energy in addition to reflected energy. In some cases, one or more elements of the imaging system 200 of FIG. 4 may be omitted.

The receive subsystem 210 may generally include a plurality of separate channels (e.g., one channel per receive transducer element, in some embodiments), each channel having an Analog Front End (AFE) 212 configured to perform various amplifying, filtering and other handling of analog signals from the probe subsystem's receive transducer elements. The AFE may be connected to an Analog-to-Digital conversion device/system (ADC) 214 which may be configured to convert received analog signals into digital signals. Such digital signals may be stored in a digital memory device such as a raw data memory device 220 as described below, and/or optionally transmitted directly 250 to elements of an image generation subsystem 230.

The image generation subsystem 230 may include a beamformer block 232 and, in some cases, may also include an image-layer combining block 234 and/or other processing blocks. The image generation subsystem 230 may generally be configured to convert the digital raw echo data received from the receive sub-system 210 or the raw data memory 220 into a series of displayable images. In some embodiments, the displayable images produced by the image generation subsystem 230 may be stored in an image buffer storage device 236. The video/image display subsystem 240 may include components such as a video processor block 242 configured to convert the series of displayable images from the image generation subsystem 230 into an analog or digital video stream that may be displayed on an output display device 244. The video/image display subsystem 240 may also include an analog or digital memory device configured to store video streams for display at a different time and/or at a different location. The image generation subsystem may also include a video memory device 246 configured to store beamformed and processed digital video files.

Any of the digital storage devices described herein, such as raw data memory devices, video memory devices, image memory devices, data warehouses and others may include any number of any suitable non-volatile digital memory device or combinations thereof. Examples of digital storage devices may include hard disk drives, solid state disk drives, flash memory devices, other solid state removable non-volatile storage devices such as SD cards or USB flash memory devices, optical storage devices such as a CDs DVDs, or Blu-Ray, magnetic tape, or any non-volatile digital memory device. In some cases, analog storage devices may also be used for data storage.

As used herein, the phrases "echo data," "raw echo data" and "raw data" may refer to stored echo information describing received ultrasound echoes at any level of processing prior to beamforming. In various embodiments, received echo data may be stored at various stages between pure analog echo signals to fully processed digital images or even digital video. For example, a raw analog signal may be stored using an analog recording medium such as analog magnetic tape. At a slightly higher level of processing, digital data may be stored immediately after passing the analog signal through an analog-to-digital converter. Further incremental processing, such as band-pass filtering, interpolation, down-sampling, up-sampling, other filtering, etc., may be performed on the digitized echo data, and "raw" output data may be stored after such additional filtering or processing steps. Such raw data may then be beamformed to determine a pixel location for each received echo, thereby forming an image. Individual still images may be combined as frames to form motion video. In some embodiments of the systems and methods described herein, it may be desirable to store digitized raw echo data after performing very little processing, e.g., after some filtering and conditioning of digital echo data, but before performing any beamforming or image processing.

Although the term "echo data" is generally used herein to refer to data received by receive elements, the term "echo data" is also intended to include data generated by digitizing received signals resulting from direct transmission of ultrasound or other transmitted energy signals without necessarily being reflected. Therefore, the phrase "echo data" may generally have the same meaning as "receive data."

In addition to received echo data, it may also be desirable to store information about one or more transmitted ultrasound signals that generated a particular set of echo data. For example, when imaging with a multiple aperture ping-based ultrasound method as described above, it is desirable to know information about a transmitted ping that produced a particular set of echoes. Such information may include the identity and/or position of one or more transmit elements, as well as frequency, amplitude (magnitude), pulse length (duration), waveform (shape), or other information describing a transmitted ultrasound signal.

Transmit data may be collectively referred herein to as "TX data". In some embodiments, such TX data may be stored explicitly in the same raw data memory device in which raw echo data is stored. For example, TX data describing a transmitted signal may be stored as a header before or as a footer after a set of raw echo data generated by the transmitted signal. In other embodiments, TX data may be stored explicitly in a separate memory device that is also accessible to any system performing a beamforming process (e.g., a PC, laptop, tablet, mobile device, server, imaging system, or other suitably configured device). In embodiments in which transmit data is stored explicitly, the phrases "raw echo data" or "raw data" may also include such explicitly stored TX data.

TX data may also be stored implicitly. For example, if an imaging system is configured to transmit consistently defined ultrasound signals (e.g., consistent amplitude, waveform shape, frequency, pulse length, etc.) in a consistent or known sequence, then such information may be assumed during a beamforming process. In such cases, the only information that needs to be associated with the echo data is the position (or identity) of the transmit transducer(s). In some embodiments, such information may be implicitly stored and extracted based on the organization of raw echo data in a raw data memory.

For example, a system may be configured to store a fixed number of echo records following each ping. In such embodiments, echoes from a first ping may be stored at memory positions 0 through 'n−1' (where 'n' is the number of records stored for each ping), and echoes from a second ping may be stored at memory positions n through 2n−1. In other embodiments, one or more empty or specially encoded records may be left in between echo sets. In some embodiments received echo data may be stored using any of various memory interleaving techniques to imply a relationship between a transmitted ping and a received echo data point (or a group of echoes). In general, a collection of data records corresponding to echoes or other signals resulting from a single transmitted ping received by a single receive element may be referred to herein as a single "echo string."

A "complete echo string" may refer to substantially all data resulting from a single ping received by a receive element, whereas a "partial string" or a "partial echo string"

may refer to a sub-set of all echoes of the single ping received by the receive element.

Similarly, a "complete data set" may refer to substantially all raw data (e.g., echoes or directly-received signals) resulting from a defined set of transmitted signals. A set of transmitted signals may be defined as an identifiable set of transmitted pings, as all pings or other signals transmitted within a defined period of time, or otherwise. A "partial data set" may refer to a sub-set of all raw data resulting from the defined set of transmitted signals.

In some cases, a complete echo string or a complete data set may comprise less than all theoretically available data, because some data may be discarded as undesirable. For example, data representing a first few milliseconds following transmission of a ping may contain substantial cross-talk or other noise that may not meaningfully contribute to a desired dataset, and may therefore be ignored. Nonetheless, the resulting dataset may still be considered a "complete echo string" or a "complete data set" if it contains all of the desired data resulting from a transmitted ping (or a set of pings). Partial echo strings or partial data sets may be obtained by selecting a sub-set of records from a complete echo string or data set in order to limit a data set for the purposes of faster data communication or limiting processing resources, for example.

Similarly, assuming data is sampled at a consistent, known sampling rate, the time at which each echo data point was received may be inferred from the position of that data point in memory. In some embodiments, the same techniques may also be used to implicitly store and organize/interpret data from multiple receive channels in a single raw data memory device.

In other embodiments, the raw echo data stored in the raw data memory device 220 may be physically or logically located in any other structure as desired, provided that the system retrieving the echo data is able to determine which echo signals correspond to which receive transducer element and to which transmitted ping. In some embodiments, position data describing the exact physical location of each receive transducer element relative to a common coordinate system may be stored in the calibration memory device 238 along with information that may be linked to the echo data received by that same element. Similarly, position data describing the exact physical location of each transmit transducer element may be stored in the calibration memory device 238 along with information that may be linked to TX data describing each ping transmitted from that transmit element.

In general, calibration data describing position and/or performance information about each transducer element may be physically located in any device electronically accessible by the device performing beamforming operations. For example, calibration data may be located in a probe device itself, in an imaging system connected by a wired or wireless connection to the probe, in a network-accessible database accessible by an imaging system, or by a server or other computing device configured to perform beamforming operations.

In some embodiments, calibration data may also include performance information. Performance information may include information identifying elements that have become damaged to the point that they provide response data that does not accurately describe the echoes impinging on the element. Depending on the nature of the inaccurate information, data from damaged elements may be ignored or weighted to minimize detrimental effects on resulting images.

In some embodiments, additional information useful in beamforming images based on stored echo data may also be stored in a digital storage device accessible to a device performing beamforming operations. Examples of such additional information may include speed-of-sound values, such as average speed-of-sound values, path-specific speed-of-sound values (e.g., a speed of sound along a ray path from a transmit aperture to a pixel/voxel location to a receive aperture), receive-aperture-specific speed-of-sound values, or others. Additional stored information may also include weighting factors or user-controllable settings used during a data-capture session.

In some embodiments, each echo string in the raw data memory device 220 may be associated with position data describing the position of the receive transducer element that received the echoes and with data describing the position of one or more transmit elements of a transmit aperture that transmitted the ping that produced the echoes. Each echo string may also be associated with TX data describing characteristics of the transmitted ping such as power level, frequency, pulse length/signal shape, emitter efficiency, etc. Such associations may be made using any suitable data structures.

In some cases, raw echo data may also be associated with various "meta-data," including information allowing a clinician or service provider to associate the raw echo data with a patient, imaging date/time, imaging location, imaging environment (ambient temperature, humidity, barometric pressure, etc.), imaging system settings used during image capture, object surface temperature, or other information that may be useful in using the raw data. Any other meta-data may also be associated with raw echo data records.

One benefit of storing raw echo data is that the information may be retrieved, processed, and reviewed at a later time, allowing a far greater degree of control and flexibility than if only a video stream (e.g., a cine loop) were saved from an imaging session. For example, in one embodiment, a patient may visit a technician and the technician may conduct an ultrasound examination during which raw echo data is captured and stored. Hours, days, weeks, or even months later (in other words, any time after the patient's original session), a trained professional such as a physician may use a personal computer, laptop, tablet or an imaging system to re-examine a wide range of images derivable from data generated during the examination session and to create new images (that is, images that were not produced during the imaging session with the patient) by manipulating the raw data without re-examining or re-imaging the patient. In some embodiments, such re-examination of stored data may include several processes that are only possible with access to raw echo data.

In some embodiments, raw data from an imaging session may be stored along with raw echo data captured while imaging a calibration phantom. For example, raw echo data obtained while imaging a calibration phantom may be used for later calibration of the imaging session data by correcting transducer element position assumptions made during live beamforming.

Information describing the position of each transducer element may be obtained by a calibration process as described in Applicants' prior applications. Such element position data may be stored in a calibration memory device 220, which may be physically located with other electronics, or may be located in a remote, network-accessible server. However, in some embodiments, the element-position information may change between performing a calibration operation and capturing raw ultrasound data. For example, a probe may have been dropped, damaged or otherwise altered before or during a raw echo data capture session.

In some embodiments, the ability to re-process stored raw echo data means that a probe may actually be retroactively re-calibrated after raw echo data is captured, and the data may be re-beamformed using the updated element position information.

In other embodiments, raw echo data stored in a raw data memory device may be analyzed to determine whether a probe is actually out of calibration.

Raw Data Capture Devices

In various embodiments, a network-based imaging system may provide the advantage of de-coupling the collection of raw echo data from formation and display of images derived from the collected raw echo data. As a result, systems operating as components in a network-based imaging system may be configured to operate in two broadly-defined modes. In a "live imaging" or "real-time imaging" mode, the system may be configured to process and display images based on echo data with as little latency as possible. Latency may be defined as the time delay between when an action (such as moving the probe relative to the object being imaged) occurs and when the imaging system displays a result of the action. Various examples of live-imaging modes are described below.

A second broad mode may be described as a "high quality data capture" mode. When a "high quality data capture" mode is initiated, a data capture component of a network-based imaging system may collect and store raw echo data (along with TX data, and other data as described herein) from a predetermined time period, number of ping cycles, or number of image cycles. During a high quality data capture mode, the full data set need not be beamformed or otherwise processed in real time. In some embodiments, the data capture device may store the raw data in an external (e.g., network-connected) storage device in real-time as it is captured. In other embodiments, such as when real-time network communication resources are limited, the data capture device may store the raw data in a local storage device in real-time, and may subsequently transfer the captured data to an external (e.g., network-connected) storage device at a later time when network resources are less constrained. A single remote data storage device or a collection of remote data storage devices may be referred to herein as a "data warehouse," which may include any number of network-connected data storage devices as needed.

Embodiments of network-based imaging systems may generally include data capture devices having lower cost and limited-performance hardware for performing transmitting, receiving and data storage functions. Data capture devices may be physically de-coupled from and located physically remotely from image generation devices which may have higher cost and higher performance hardware and/or software for performing beamforming and image processing functions. Some embodiments of network-based imaging systems may also include end-use viewer terminals in network-communication with the image generation devices and/or in communication directly with one or more data capture devices. Such viewer terminals may be used for real-time or time-shifted viewing of images generated from captured raw data. In some embodiments, data capture devices may be configured for operation by relatively minimally-trained technicians who may be guided by one or more highly trained professionals via network communications or by a software or artificial intelligence agent.

In some embodiments, raw echo data that is captured and stored in a raw data memory device as described above may subsequently be copied, forwarded, or otherwise electronically communicated to an external (e.g., a backup) memory storage device. Such data communications may take place over any available wired or wireless data transfer system, such as Bluetooth, IR/Infra-Red, USB, IEEE 1394 Firewire, Thunderbolt, Ethernet/Intranet/Internet (TCP/IP, FTP, etc.) or others.

In some embodiments, the raw data may be loaded back onto an ultrasound imaging system (e.g., the same system originally used for insonification and raw echo data capture), or a similarly-configured ultrasound imaging system for re-processing, re-beamforming, and image generation/viewing. In other embodiments, a personal computer, laptop, tablet, mobile device, network-connected server, or other digital computing device may be configured with software and/or hardware to beamform and/or process the raw echo data into images without the use of a dedicated ultrasound imaging system.

In other embodiments, raw echo data may be beamformed, processed and displayed by software on any other suitably configured computational device or system, such as a tablet or smart phone. In other embodiments, raw echo data may be uploaded over a network to a network-accessible server which may store and process image data remotely.

Figure 5:
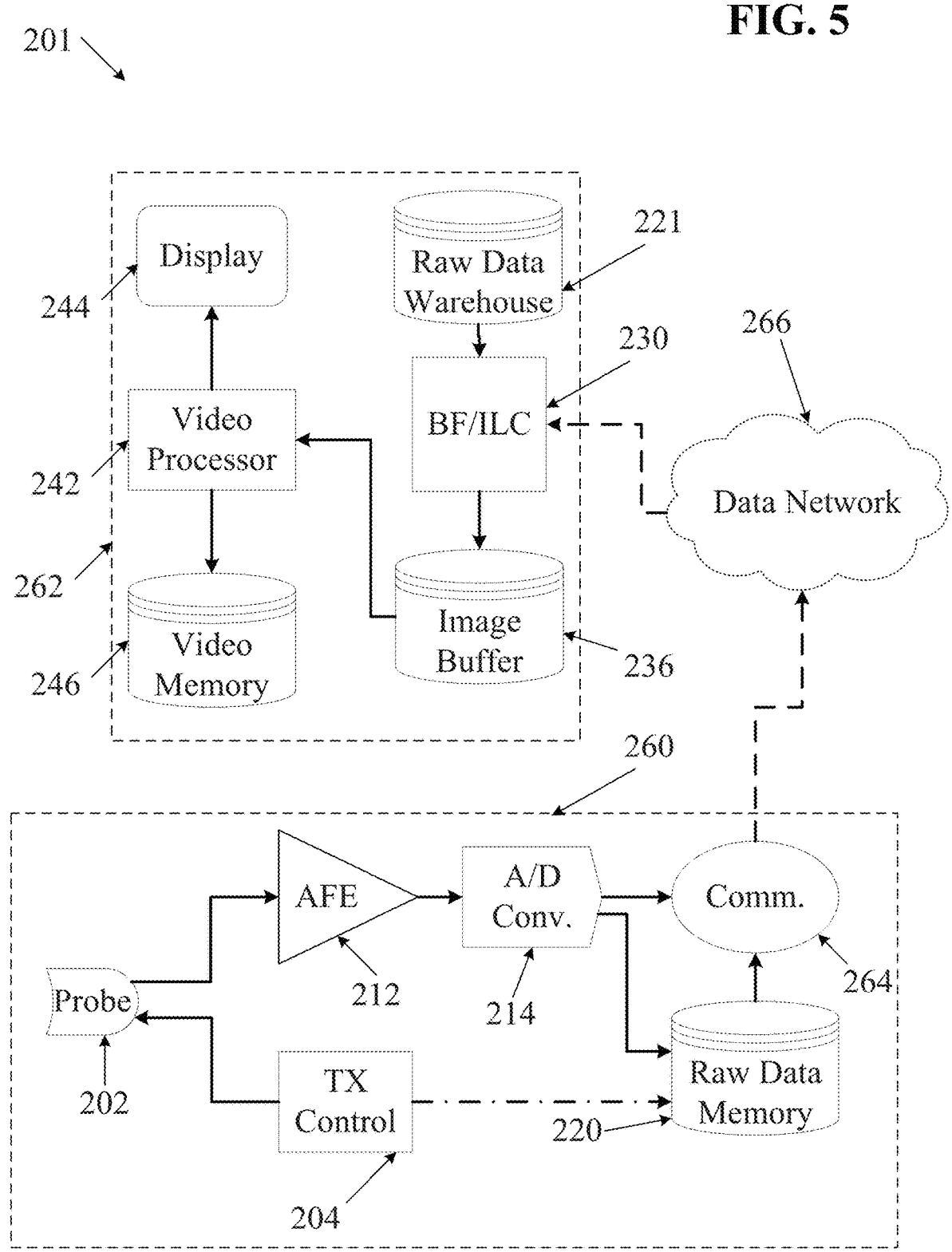
FIG. 5 is a schematic illustration of an embodiment of a network-based imaging system.

FIG. 5 illustrates an embodiment of an imaging system 201 divided into an energy (e.g., ultrasound) data capture and communication device 260 and a remote image generation and display system 262. The data capture and communication device 260 may be configured with minimal hardware components for communication of raw echo data to the remote imaging system 262 via a communications device 264 and a wired or wireless network 266.

The data capture device 260 of FIG. 5 may include a probe 202, a transmit controller 204, an AFE 212 and an ADC 214 as described above. In place of any beamforming or image processing components, the data capture device 260 may instead include a communications device 264 configured to communicate raw echo data to a remote system 262 via a network 266. The remote system 262 may include hardware, firmware and/or software configured to beamform and process the raw echo data captured by the device 260.

In some embodiments, the probe 202 may be an ultrasound probe with ultrasound transducer elements spaced from one another in two or three dimensions and configured for capturing 3D volumetric ultrasound data as described herein.

In some embodiments, the communications device 264 may be configured to stream raw echo data in real time to the remote system 262. In other embodiments, the data capture device 260 may include an internal memory device 220 for short term storage of raw echo data (e.g., as a communication buffer). In other embodiments, an internal memory device 220 within the data capture and communication device 260 may be configured for longer term storage of raw echo data within the capture device 260. In further embodiments, a data capture device may contain one, two or more memory devices 220 configured for various uses.

For example, a data capture and communication device 260 may include a first memory device 220 configured to operate as a circular buffer for storing real-time data immediately prior to communicating the real-time data over a network 266. After data has been communicated from the device 260, the data may be deleted or overwritten with newly acquired data. The data capture device 260 may also contain a second memory device configured to operate as a circular buffer for a full set of raw echo data to be communicated over the network in response to a command from an operator.

In some embodiments, a system 201 such as that shown in FIG. 5 may be used in an environment in which an operator of the data capture device 260 does not require a display, such as when using a probe configured to be placed in a stationary position on a patient during a data capture session. In some cases, a third party (e.g., in addition to the patient and the data capture device operator) may view real-time images produced from the raw echo data obtained by the data capture device 260 and communicated over the data network 266. The third party reviewing the images may then provide real-time instructions relating to the placement of the probe on a patient or other object to be imaged. In some embodiments, such positioning instructions may be delivered verbally, such as over a telephone or other audio connection. Alternatively, probe placement instructions may be communicated to the operator by way of indicators on the probe itself or by an external device such as a display screen or other device.

For example, a tablet device with an integrated camera may be used to produce an optical image of the patient or other object with the probe 202 in place. The tablet may include an application configured to indicate a direction and distance of movement of the probe on the patient (or other object) to a more ideal location. Such movement instructions may be provided by a third-party viewing images at a remote image generation and display system 262. Alternatively, probe positioning instructions may be provided to the operator by an artificial intelligence application on the tablet or by directional indicators on an image being displayed on a tablet or other display screen.

In some embodiments, some or all elements of a remote image generation and display system 262 may be implemented in a tablet, personal computer, laptop, mobile device, or a combination of such elements, collectively referred to herein as a "control surface". For example, in some embodiments, image generation, raw data storage and image buffering functions may be performed in a computing device which may be in wired or wireless communication with a control surface such as a handheld tablet device which may be configured to perform the display and video processing functions along with user interface functions.

Figure 6:
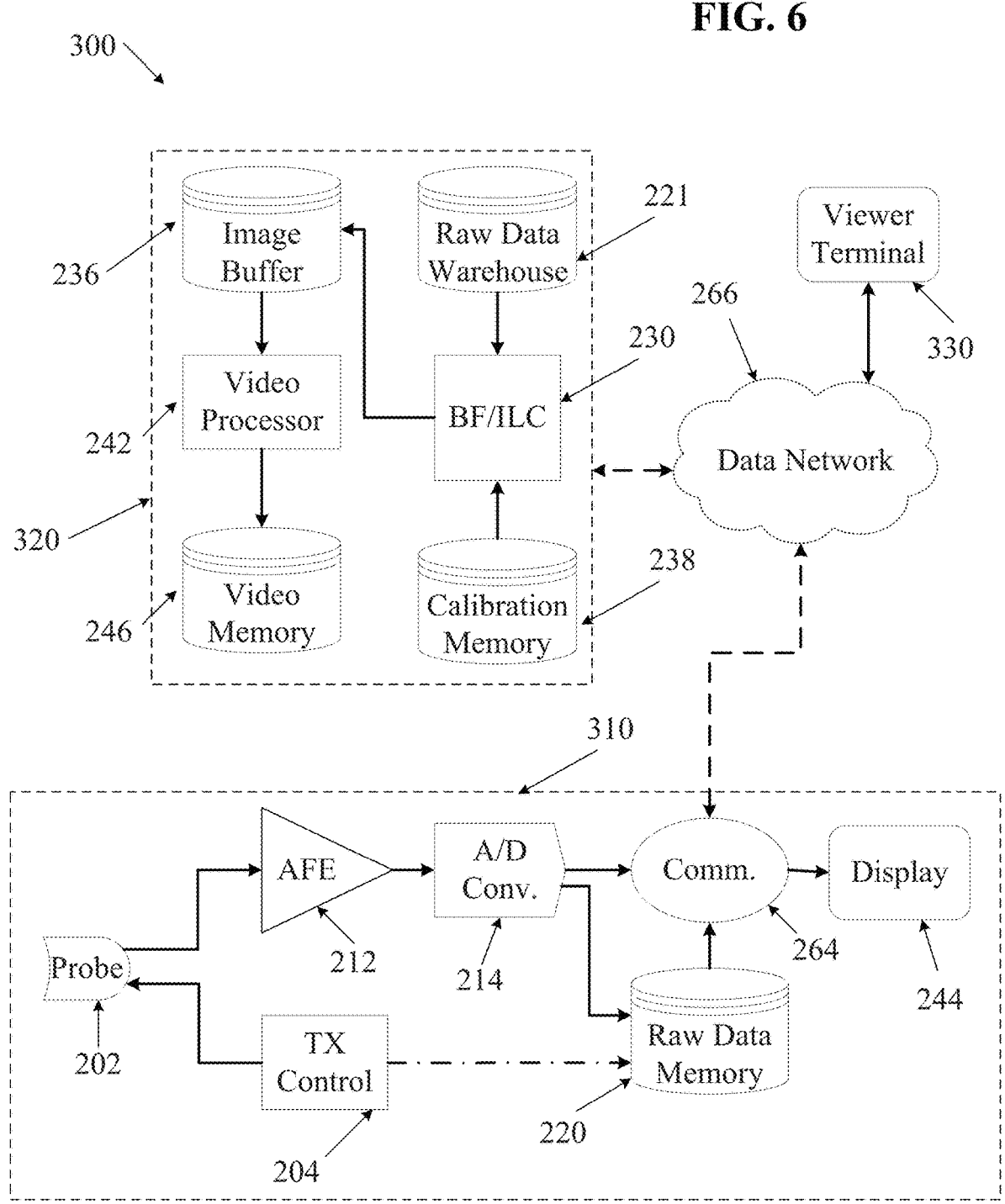
FIG. 6 is a schematic illustration of another embodiment of a network-based imaging system.

FIG. 6 illustrates another example of an imaging system 300 comprising a limited function data capture and communication device 310, a network-based beamforming and video processing device 320, and one or more viewer terminals 330 connected to one another via a wired or wireless data network. As shown in the illustrated example, the data capture and communication device 310 may include a probe 202, a transmit controller 204, an AFE, 212, an ADC 214, a raw-data memory device 220, a communications device 264, and a display 244. In some embodiments, the probe 202 may be an ultrasound probe with ultrasound transducer elements spaced from one another in two or three dimensions and configured for capturing 3D volumetric ultrasound data as described herein.

The network-based beamforming and video processing device 320 may include one or more digital storage devices comprising a raw data warehouse 221, an image generation subsystem 230 which may include hardware and/or software for performing beamforming, image layer combining (as described above, for example) and other image generation processes. The beamforming and video processing device 320 may also include a calibration memory 238, an image buffer 236, a video processor 242, and a video memory 246.

In operation, the imaging system 300 may be used for live real-time imaging of a patient or object to be imaged. An example of a real-time imaging process is described below with reference to FIG. 7. Live real-time imaging may be performed using the limited function data capture and communication device 310 by using the probe 202 to transmit ultrasound pulses into the region of interest (such as unfocused three-dimensional pings) and receive echo signals from the region of interest. The received signals and other information (e.g., calibration information, TX data, device identifier, etc.) may be communicated from the data capture and communication device 310 to the beamforming and video processing device 320 over the network 266. The beamforming and video processing device 320 may beamform the echo data to generate images and may produce data representing a video stream that may be electronically communicated over the network 266 back to the data capture and communication device 310 for display to an operator on the display 244 of the device 310.

The data capture and communication device 310 of FIG. 6 may include a probe configured to transmit into and receive energy from an entire three-dimensional volume to be imaged. Alternatively, the data capture and communication device 310 of FIG. 6 may include a probe configured to insonify and receive echoes from only a single imaging plane. In some embodiments, the data capture and communication device 310 of FIG. 6 may be configured with beamforming hardware and software omitted. This may allow for the data capture and communication device 310 to be constructed at relatively lower cost, and utilize components with relatively lower power demand. In some embodiments, several such low-cost data capture and communication devices 310 may be deployed within a local network (such as a hospital, medical center, imaging center, or other facility in which imaging may be performed). All such devices may utilize the same beamforming and video processing device 320 over the local network. In some embodiments, the beamforming and video processing device 320 may comprise several servers in order to manage a load of several simultaneous live imaging sessions.

In order to conduct live, real-time imaging sessions using a network-based imaging system, it may be desirable to limit the quantity of raw echo data to be processed to form real-time images. The quantity of raw echo data to be processed and/or communicated over a network may be reduced by using one or more of various data reduction methods. Some examples of which are provided below.

In the case of a network-based beamformer such as that illustrated in FIG. 5 and FIG. 6, various data reduction methods may be used to reduce the quantity of data communicated over the data network 266 from each data capture and communication device 310 to the beamforming and video processing device 320.

One example data reduction approach may involve identifying a reduced set of data samples to be processed into images by defining a limited image window. In some embodiments, the quantity of raw echo data to be processed and/or communicated over a network can be greatly reduced by determining a minimum sample window necessary to generate images of a defined image window.

An image window may be defined as a particular two-dimensional plane (possibly as a portion of a three-dimensional volume), qualified by zoom level, and further constrained by left-right pan and up-down elevation within the insonified object's region of interest. An image window may be selected automatically by the data capture and communication device 310, manually by an operator of the device, or a combination of manually and automatically.

As used herein, the term "sample window" may refer to a range or list of sample index values identifying a set of stored data samples meeting some criteria. For example, a sample window may be defined as the set of data samples corresponding to pixels of a two-dimensional image window which may be defined in terms of size, position, and orientation within an insonified volume.

In some embodiments, a process for reducing a data set by image window sample selection may comprise the steps of (1) defining an image window, (2) identifying receive data samples corresponding to the defined image window, and (3) selecting only those samples corresponding to the defined image window for processing or communication over a network.

In some embodiments, an optimum set of raw data samples (earliest through latest per ping for each receive element) needed for generating a particular image window may be determined by calculating the sample numbers (or other sample-identifying indices) corresponding to the top and bottom rows of image window pixels, and communicating only those reduced ranges of samples to the remote beamforming and video processing device 320; all raw data samples outside of these ranges will not be used for beamforming that particular image window, so need not be communicated to the remote beamforming and video processing device 320. Typically, and depending on zoom level selected, only a quarter or fewer of the total samples collected per ping for each receive element may be used during the beamforming process. Each TX-RX pair may generate a slightly different range of necessary samples for a given image window, but the variation among all pairs may be small enough to simply use the minimum 'early' sample number/index through the maximum 'late' sample number/index across all pings and receive elements.

One data reduction technique may include using a process for directly beamforming a two-dimensional image from raw data produced by insonifying a three-dimensional volume, as described above with reference to FIG. 1. In such embodiments, a reduced data set may comprise only the data corresponding to the selected two-dimensional image plane, while a "complete" raw data set may comprise echo data received from the entire three-dimensional volume.

A set of data samples to be processed or communicated over a network may be further reduced by effectively reducing a frame rate of a displayed video stream. Frame rate reduction may be performed in multiple ways. For example, in some embodiments a frame rate may be reduced by selecting only echoes of selected pings for processing into image frames. In other words, a size of a raw data set may be reduced by using the data produced by less-than-all transmitted pings. For example, if only the echoes of every-other transmitted ping are selected for processing, then the data set may be reduced by half. In other examples, selected data may be limited to data received from every third ping, every fourth ping, every fifth ping, etc.

In another example, raw data may be selected based on the position and/or identity of transmit elements that produced the data. For example, if a probe contains X transmit apertures (or transmit elements where each transmit aperture has only one element), each of which transmits a ping during a typical imaging cycle, then a data set to be processed or communicated over a network may be reduced by selecting only echo data samples corresponding to pings transmitted by X/2, X/3, X/4, X/5, etc. of the transmit elements. In some embodiments, the transmit elements from which echo data is to be selected may be chosen based on position of the elements in the probe. For example, if only a small region under the probe is of interest, then chosen transmit elements may be limited to those above the small region of interest.

In other embodiments, a data set may be reduced by pre-combining echo data before processing or communicating the data over a network. For example, receive data received by the same receive element in response to two separate pings may be combined with one another coherently, thereby reducing two data points to one. In some embodiments, a first echo string received by a first receive element resulting from a first ping may be coherently combined with a second echo string received by the first receive element resulting from a second ping. In some embodiments echoes of two or more pings received by the same element may be combined before performing other data reduction methods.

Many other methods may be used for reducing the set of raw echo data to be transferred when conducting live, real-time imaging sessions using a network-based beamformer and image generation device 320. In one example, the real precision of the A/D Converter 214 may be closely measured, and the LSB (Least Significant Bit) bits that correspond most closely to sampling noise, conversion noise, or quantization error may be stripped or removed from the data to be transferred. For example, for a 16-bit ADC with sufficiently high statistical error probabilities in bits 0 through 2, it may be sufficient to only communicated bits 3 through 15 and pack sequential samples accordingly, reducing bandwidth needs by nearly 20%.

Another data reduction method may include reducing the frame rate of communicated data to a small fraction of the full frame rate supported by the Analog Front End (AFE) or other electronics, with a corresponding linear reduction in bandwidth needs.

Another data reduction method may include, prior to communicating a reduced set of data samples over the network 266, compressing the raw data samples of the set using a lossless or lossy compression algorithm as requirements dictate, allowing for another potential 25% to 75% or greater reduction in bandwidth needs.

Another data reduction method may include reducing a total number of receive elements for which data is selected. For example, a subset of all receive elements may be selected, and receive data from only those selected elements may be selected for beamforming or communication over a network. In some cases, a subset of receive elements may be selected based on position of the receive elements relative to a particular feature of interest within an insonified volume. In other cases, the number of elements assigned to an aperture may be reduced, such as by ignoring some receive elements in between selected elements, using only data from the selected elements.

In other embodiments, entire apertures may be ignored, such as by selecting some apertures to be included in a reduced data set, while removing data from one or more apertures. In some embodiments, data received by a group of elements between selected apertures may be removed from a data set to form a reduced data set.

In some cases, several data reduction techniques may be applied concurrently, yielding compounded reductions in total communicated data.

In some cases, a level of data reduction to be applied may be based on a desired image quality level for a particular imaging application. For example, if a user or an automated system determines that a particular imaging application requires a high quality real-time image, then data reduction methods may be selected based on their impact on image quality in order to preserve image quality at a minimum level needed for the identified application. On the other hand, if a lower image quality is acceptable for an identified imaging application, then data reduction methods that may tend to reduce image quality may be used.

In some embodiments, the data capture and communication device 310 may include a user interface with controls allowing an operator to select an image window, adjust imaging parameters, and capture raw echo data to local and/or remote storage for later review and analysis. Capturing raw data may comprise storing raw echo data received by the transducer elements during several seconds (or more) of imaging. The raw data captured may be stored in the raw data memory device 220 in the data capture and communication block 310, and may be communicated to the remote beamforming and video processing block 320 over the network 266 and stored in the raw data warehouse 221.

In some cases, in addition to data reduction, various processing-reduction adjustments may be made to beamforming, image layer combining, or image processing methods. For example, performing fewer data combining (image layer combining) steps may reduce a quantity of processing needed to produce each image frame. Similarly, by adjusting a balance of coherent vs incoherent summation of image layers, a number of processing cycles to produce an image frame may be increased or decreased. In other embodiments, any other processing-reduction methods may be used.

The raw data captured and stored by the data capture and communication device 310 may include substantially all of the received data, without reducing or reducing the data using the techniques described above. This allows the raw data set to be used for more detailed review and analysis than might be available for real-time imaging with a limited-function data capture and communication device 310.

In some embodiments, the system of FIG. 6 may be used in combination with a viewer terminal 330, such as a laptop computer, a desktop computer, a tablet, a smartphone, or other computing device configured to connect to the remote image generation system. For example, an operator controlling the probe 202 may view a video stream produced by the video processing block 320 on a terminal device 330 instead of (or in addition to) the display 244.

Figure 7:
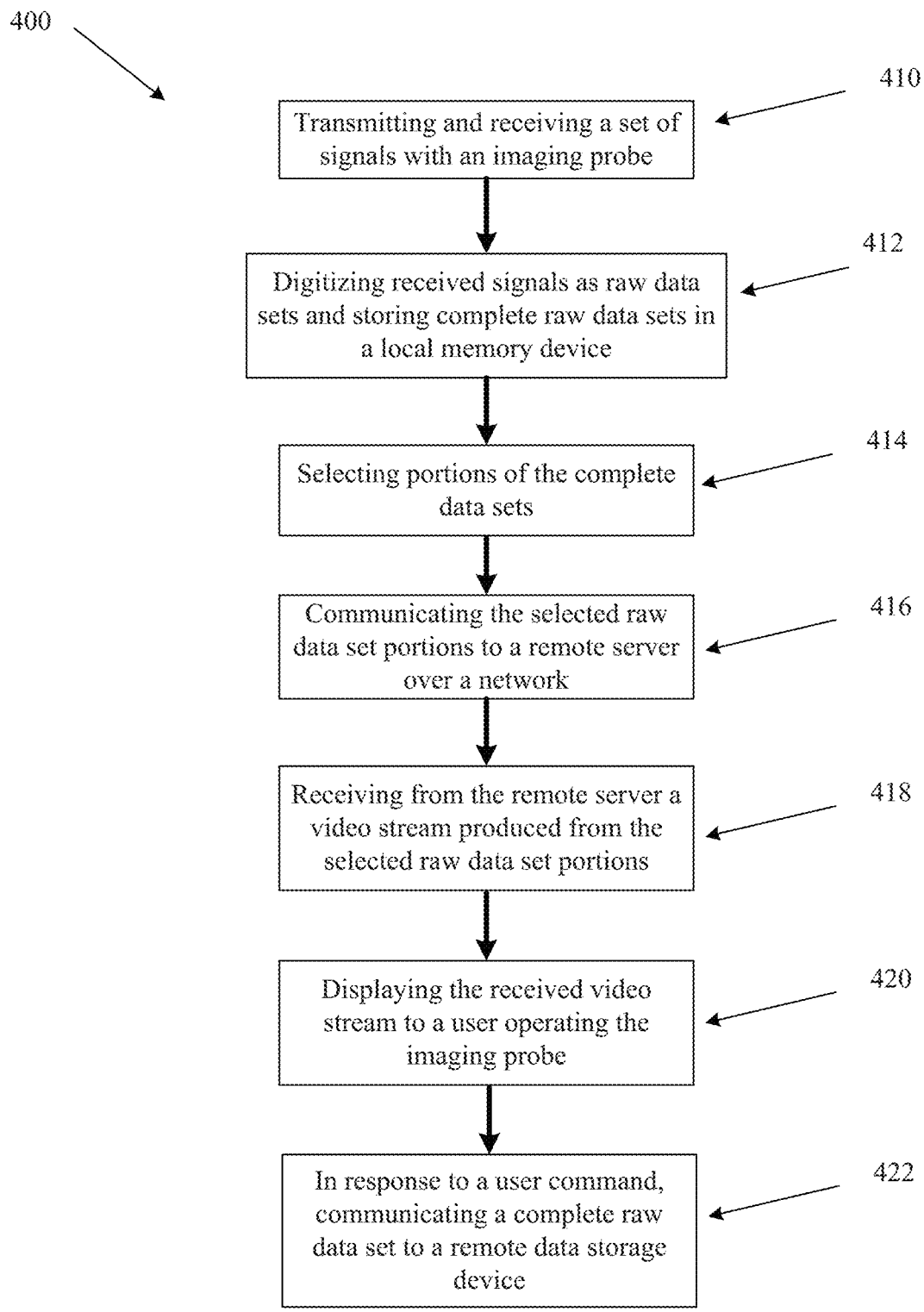
FIG. 7 is a process flow diagram illustrating an example embodiment network-based imaging process.
Figure 8:
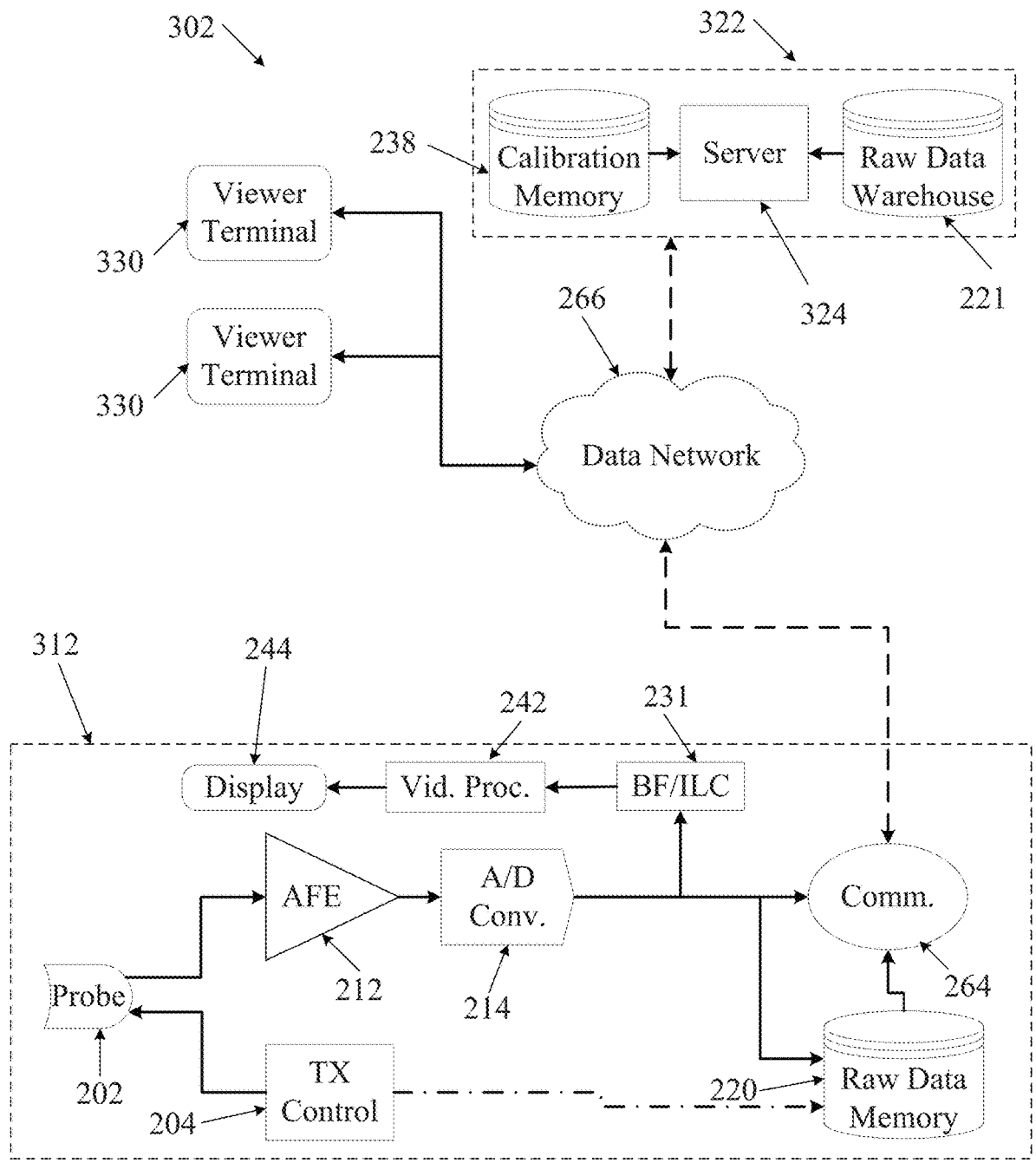
FIG. 8 is a schematic illustration of another embodiment of a network-based imaging system.

FIG. 7 illustrates an example of a network-based imaging process 400 that may be performed by a raw data capture device, such as those described herein (e.g., the device 260 of FIG. 5, the device 310 of FIG. 6, the device 312 of FIG. 8, or any other suitably configured device). In various embodiments, the steps of the process 400 of FIG. 7 may be performed by two or more devices.

The process 400 of FIG. 7 may generally be configured to perform a live imaging process while communicating a limited data set to a remote server (e.g., 262 of FIG. 5, 320 of FIG. 6, or 322 of FIG. 8) which may perform beamforming operations and communicate a video stream back to the data capture device and/or an adjacent display device (such as a laptop, PC, tablet, mobile device, or other control surface). In various embodiments, user interface elements may be provided in the data capture device, in a separate control surface device, or in another device.

The process 400 of FIG. 7 may include transmitting and receiving signals with an imaging probe as shown in block 410. In some embodiments, the operations of block 410 may include transmitting and receiving steps as described herein with reference to ping-based multiple aperture imaging. Alternatively, transmitting and receiving signals may include any other suitable imaging process. Any suitable probe device may be used.

At block 412, the process 400 may include digitizing received signals as raw data sets and storing complete raw data sets in a local memory device. As described herein, digitizing received signals may be performed with any suitable analog front end, analog-to-digital conversion, and/or other hardware and software components. The local memory device may be any suitable volatile or non-volatile memory device.

As described above, a "complete data set" may refer to substantially all raw data (e.g., echoes or directly-received signals) resulting from a defined set of transmitted signals. A set of transmitted signals may be defined as an identifiable set of transmitted pings, as all pings or other signals transmitted within a defined period of time, or otherwise. Thus, for example, a complete data set may include all digitized received signals resulting from a set of X transmitted pings, where X is any number from 1 to 1 million or more (practical systems may define sets of pings based on a number of transmit elements of a probe, for example).

At block 414, the process 400 may include selecting portions of the complete stored raw data set for communication over the network. Selecting portions of the data sets may include any one or more of the data reduction methods described above. For example, in some embodiments, a selected reduced data set may comprise only data corresponding to a selected two-dimensional image plane, while a "complete" raw data set may comprise echo data received from the entire insonified three-dimensional volume.

At block 416, the process 400 may include communicating the selected raw data set potions over a network to a remote server. As described herein, the network may include any data network, and the remote server may include any suitable server device. In some embodiments, the remote server may be physically located a distance of several miles or more from the probe, while in other embodiments, the remote server may be located in the same room. The server may only be "remote" in the sense that it is not housed in the same device as the data capture device.

The remote server may process the received information and beamform the raw data set portions to produce images which may be combined to form a video stream. The methods used by the remote server may include any beamforming, image layer combining, and/or other image processing techniques appropriate for the received data, including the various example methods described herein.

At block 418, the process 400 may include receiving a video stream from the remote server over the network. The video stream may be communicated using any suitable digital video communication protocols or methods. At block 420, the received video stream may be displayed to an operator of the imaging probe (who may also be operating the data capture device).

At block 422, the process 400 may include, in response to a user command to initiate a "high quality data capture mode" as described herein, communicating a complete raw data set over a network to a remote data storage device. As described in various examples above, the remote data storage device may be integral with or separate from the same remote server used to perform beamforming and image processing. The network used for communicating the complete raw data set may be the same network or a different network than the one used to communicate the selected raw data set portions. In various embodiments, the complete data set may be retrieved from the remote data storage device, beamformed and processed into images in near-real-time (e.g., within second or milliseconds of it being received at the remote data storage device) or at any longer time delay.

In various embodiments, each viewer terminal 330 may include independent user interface controls configured to independently control imaging parameters. Independently-controlled imaging parameters may include any items of user-controllable information affecting an image displayed to the user. For example, imaging parameters may include beamforming parameters such as speed-of-sound and image window selection, or video processing parameters such as brightness, contrast, video filters, etc.

FIG. 8 illustrates an example of an alternate configuration of an imaging system 302 with a limited-function data capture and communication device 312 in communication with a network-based remote image generation system 322. The data capture and communication device 312 may optionally include hardware and software elements to enable the device to perform some or all beamforming and image generation operations locally and to display a limited-quality (and/or lower frame rate) real-time image to an operator. The data capture and communication device 312 may also be configured to communicate full-quality raw echo data from the full insonified 3D volume or 2D plane to the network-based image generation system 322 for real-time and/or time-shifted manipulation and viewing by one or more remote professionals (e.g., physicians, sonographers, or other trained professionals) using a viewer terminal 330.

The data capture and communication device 312 may include a probe 202 (e.g., a 3D imaging probe or a 2D imaging probe as described above), a transmit controller 204, an AFE 212, an ADC 214, a raw data memory device 220, a communication device 264, an image generation block 231 which may perform beamforming and image layer combining operations, a video processor 242, and a display 244. In some embodiments, the data capture and communication device 312 may include components with relatively low processing power and low power requirements in order to allow an operator to see a limited-quality real-time image, while allowing for full-quality data to be captured, stored and communicated to a raw data warehouse 221.

The data capture and communication device 312 of FIG. 8 may include a probe configured to transmit and receive energy in an entire three-dimensional volume to be imaged. In some embodiments, the image generation block 231 may be configured to beamform echoes received from a single plane within a three-dimensional insonified volume, while optionally (e.g., on an operator's command) storing several seconds worth of raw echo data from the full 3D volume in the on-board raw data memory 220 and/or communicating the 3D volumetric raw data to the raw data warehouse 221.

In order to limit the hardware requirements for the data capture and communication device 312, on-board real-time beamforming and image generation and display hardware may be limited to generating and processing images for one or more two-dimensional slices within an insonified 3D volume. In some embodiments, the 2D slice (or slices) to be beamformed and displayed may be selected manually by an operator. In other embodiments, the displayed image planes may be fixed for a particular probe, or may be automatically selected by software. Fixed planes, for example, may include a pair of orthogonal planes intersecting at the center of a probe array (e.g., the plane 150 in FIG. 3 and a vertical plane orthogonal to plane 150), plus a horizontal plane orthogonal to the two vertical planes. Fixed planes may include axial, corneal, sagittal, transverse and other planes commonly used in anatomical imaging. These two or more planes may be displayed side-by-side on the display 244. Alternatively, two, three, four or more user-selectable (and not necessarily orthogonal) planes may also be displayed simultaneously.

Additionally, the amount of processing to be performed by the image generation block 231 may be limited by utilizing any of the data reduction methods described above, such as producing images at a frame rate substantially lower than a maximum frame rate that may be achievable with ping-based multiple aperture imaging.

The system of FIG. 8 may also be used in combination with a viewer terminal 330, such as a laptop computer, a desktop computer, a tablet, a smartphone, or other computing device configured to connect to the remote image generation system in order to allow the full-quality image data to be viewed by the operator either in real-time or after the imaging session has been completed.

In some embodiments all or a substantial portion of the raw data collected by a data capture device may be communicated to the remote image generation system 322 in real-time (or as close to real-time as possible). In such embodiments, one or more remote users may view near real-time images of the imaging session via a network-connected viewer terminal 330.

The remote image generation system 322 may include a calibration memory device 238, a raw data warehouse 221, and an image processing server 324. The image processing server may include hardware and software elements suitable for performing any of the sub-processes described herein, such as beamforming, image layer combining, image process, video processing, etc. The image processing server 324 may also be configured to retrieve raw data from the raw data warehouse and corresponding calibration data from the calibration memory based on a request from a user operating a viewer terminal or a data capture and communication device 312 for an identified imaging session.

In some embodiments, the remote user may select one or more image windows entirely independent of an image window (if any) being viewed by an operator of the data capture and communication device 312. Similarly, the remote user may adjust beamforming and image generation parameters independently of settings used by an operator of the data capture and communication devices 312 without necessarily changing an image displayed to the operator. Variables that may be adjusted by the remote viewer user may include speed-of-sound values, zoom level, pan window, weighting factors, image layer combining algorithms, etc.

In addition to ping-based beamforming, beamformer technology may be separately packaged for embedding into a scanline-based imaging system or installed on a server and made available to scanline-based imaging systems through a network connection. In some embodiments, a data capture device may comprise a tap configured to intercept electrical signals sent to and received from a conventional ultrasound (or other) imaging probe.

Figure 9:
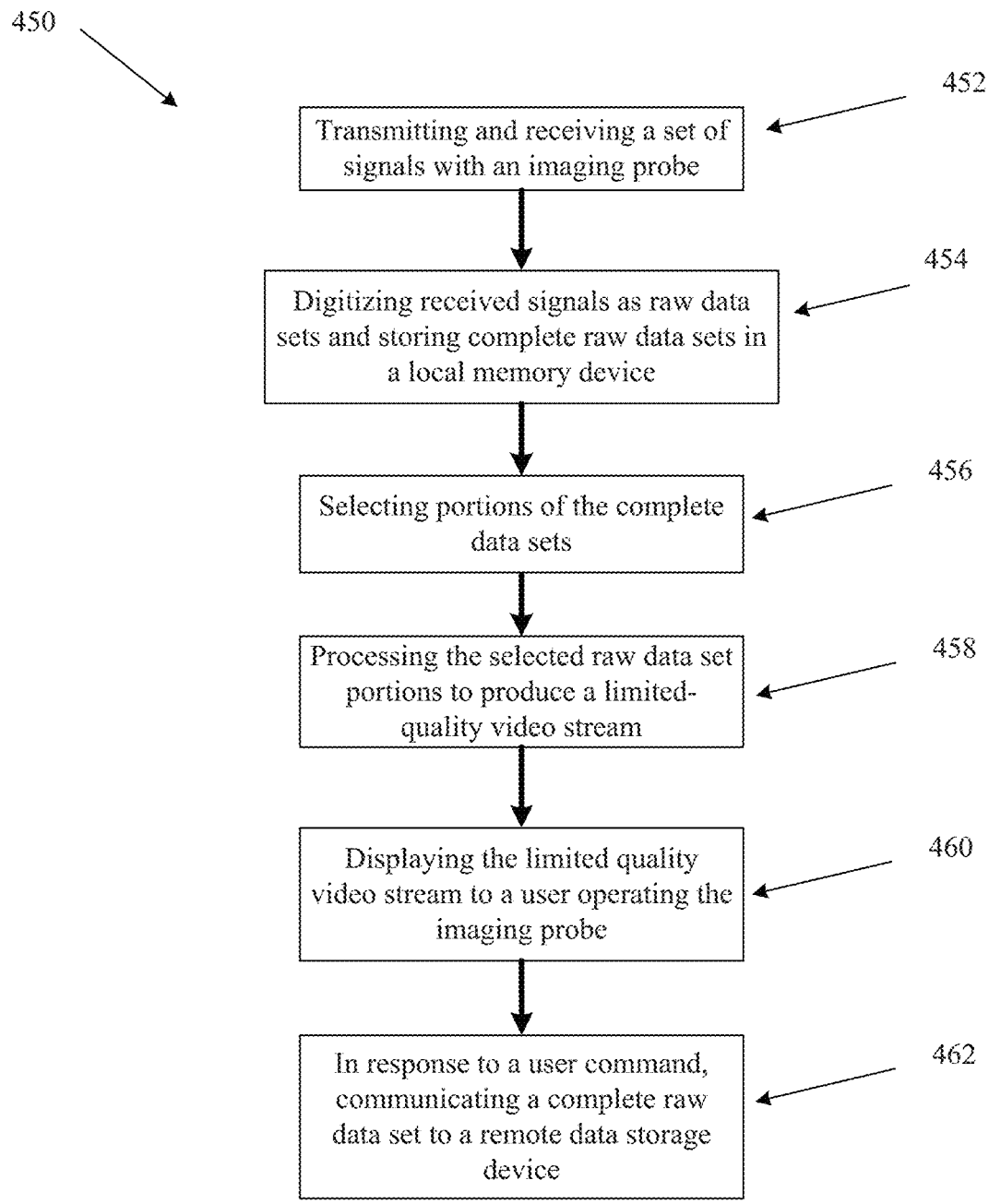
FIG. 9 is a process flow diagram illustrating an example embodiment network-based imaging process.

FIG. 9 illustrates an example of a network-based imaging process 450 that may be performed by a raw data capture device that includes at least some beamforming and imaging processing electronics, such as the device 312 described herein with reference to FIG. 8. In various embodiments, the steps of the process 450 of FIG. 9 may be performed by two or more devices.

The process 450 of FIG. 9 may generally be configured to perform a live imaging process using a built-in processor to beamform and process a limited data set and display a limited-quality video stream while capturing and storing a complete data set from which a full-quality video stream may be produced. On command, the complete data set may be communicated over a network to a remote storage device. In various embodiments, user interface elements may be provided in the data capture device, in a separate control surface device, or in another device.

The process 450 of FIG. 9 may include transmitting and receiving signals with an imaging probe as shown in block 452. In some embodiments, the operations of block 452 may include transmitting and receiving steps as described herein with reference to ping-based multiple aperture imaging. Alternatively, transmitting and receiving signals may include any other suitable imaging process. Any suitable probe device may be used.

At block 454, the process 450 may include digitizing received signals as raw data sets and storing complete raw data sets in a local memory device. As described herein, digitizing received signals may be performed with any suitable analog front end, analog-to-digital conversion, and/or other hardware and software components. The local memory device may be any suitable volatile or non-volatile memory device.

As described above, a "complete data set" may refer to substantially all raw data (e.g., echoes or directly-received signals) resulting from a defined set of transmitted signals. A set of transmitted signals may be defined as an identifiable set of transmitted pings, as all pings or other signals transmitted within a defined period of time, or otherwise. Thus, for example, a complete data set may include all digitized received signals resulting from a set of X transmitted pings, where X is any number from 1 to 1 million or more (practical systems may define sets of pings based on a number of transmit elements of a probe, for example).

At block 456, the process 450 may include selecting portions of the complete stored raw data set for real-time beamforming and image processing. Selecting portions of the data sets may include any one or more of the data reduction methods described above. For example, in some embodiments, a selected reduced data set may comprise only data corresponding to a selected two-dimensional image plane, while a "complete" raw data set may comprise echo data received from the entire insonified three-dimensional volume.

At block 458, the selected raw data set portions may be processed and beamformed to produce a limited-quality video stream. The image processing block 231 and the video processing block 242 within the data capture and communications device 312 may beamform and process the selected raw data portions to produce images which may be combined to form a limited quality video stream. The methods used by the image processing block 231 may include any beamforming, image layer combining, and/or other image processing techniques appropriate for the selected data, including the various example methods described herein.

At block 460, the limited quality video stream may be displayed to an operator of the imaging probe (who may also be operating the data capture and communications device 312).

At block 462, the process 450 may include, in response to a user command to initiate a "high quality data capture mode" as described herein, communicating a complete raw data set over a network to a remote data storage device. As described in various examples above, the remote data storage device may be integral with or separate from the same remote server used to perform beamforming and image processing. The network used for communicating the complete raw data set may be the same network or a different network than the one used to communicate the selected raw data set portions. In various embodiments, the complete data set may be retrieved from the remote data storage device, beamformed and processed into images in near-real-time (e.g., within second or milliseconds of it being received at the remote data storage device) or at any longer time delay.

The retrieved complete data set may be processed by the image processing server 324 to produce a video stream of higher quality than the limited quality video stream. The retrieved complete data set may also be processed by the image processing server 324 to produce entirely different images and/or video than what was viewed in real-time by the operator of the data capture device.

Remote-Guided Imaging

In some embodiments, an operator of a limited-function data capture and communication device such as those described above may be remotely guided in positioning the probe on a patient or other object by a more-skilled operator. Alternatively, or in addition, probe-positioning guidance may also be provided by an automated system.

In various embodiments, automatic guidance may be provided by an artificial intelligence system utilizing computer aided detection techniques to recognize features within an image and suggesting probe movements to more fully capture a desired target object. Alternatively, automatic guidance may be provided by obtaining optical images of the probe as positioned on a patient (or other object). Such optical images may be obtained with a web-cam or other computer-connected digital camera. Artificial Intelligence software configured to recognize anatomical features may be used to guide the user to place the probe in an ideal position for imaging a target organ or other object. In some embodiments, a laser pointer or other indicator may be used to indicate probe movement instructions to the operator.

Alternatively, the operator may be guided by a static or dynamic image of a mannequin mock-up of a patient with illustrations of where to place the probe in order to image a desired organ or other object.

Data Communications and Storage

In various embodiments, the systems of FIG. 5-FIG. 8 may be configured to communicate information in addition to the raw echo data to a network-based storage device. For example, the systems may communicate various annotations and/or header information along with the raw echo data. Such annotation/header data may include information allowing a clinician or service provider to associate the raw echo data with a patient, such as an anonymized patient ID number. Additionally, information such as a date/time of the data capture session, a location of the data capture session, imaging system settings used during image capture, a probe identifier, calibration data, environmental data, or other information that may be useful in beamforming or otherwise using the raw data.

Some examples of data reduction procedures are described above. In addition to those methods, additional processes may be performed to package, compress, annotate or otherwise modify raw echo data prior to transmission to the data warehouse.

In some embodiments, each probe may be provided with its own hard-coded globally unique identifier (GUID). The GUID, combined with the numerical representation of the current date and time may be used as a basis for creating a unique identifier for each data capture session. The unique identifier may then be associated with the header data associated with and stored with the raw echo data from the data capture session. The header data may include elements such as: the date and time of the data capture, the geographic location of the data capture, an ID number identifying the patient (or other object to be imaged), the settings of the probe, user interface settings used during live imaging, and any other pertinent information. The unique identifier and header information may be associated with the raw data set and stored locally and/or in a data warehouse. The stored information may be referenced at any point in the future for an unlimited amount of accesses.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. Also as used herein, unless explicitly stated otherwise, the term "or" is inclusive of all presented alternatives, and means essentially the same as the commonly used phrase "and/or." It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. A method of ultrasound imaging comprising:
   transmitting an unfocused three-dimensional ping into an object from a transmitter element of a transducer array in a probe of a data capture device;
   receiving echoes of the unfocused three-dimensional ping with a plurality of receiver elements of the transducer array;
   converting analog signals from each of the plurality of receiver elements into a full dataset of digital sample sets, wherein the full dataset comprises digital sample sets from all the receiver elements;
   beamforming a sub-set of the digital sample sets locally with the data capture device to form a limited quality video stream, wherein the sub-set comprises fewer digital samples than the full dataset;
   displaying the limited quality video stream on a first display coupled to the data capture device;
   communicating the full dataset to a network-based image generation system;
   beamforming the full data set with the network-based image generation system to form a high quality video stream; and
   displaying the high quality video stream on a second display coupled to the network-based image generation system.

2. The method of claim 1, further comprising communicating the full dataset with a wired or wireless data transfer system.

3. The method of claim 1, wherein the network-based image generation system is selected from the group consisting of a tablet, a personal computer, a laptop, and a mobile device.

4. The method of claim 3, wherein the limited quality video stream is displayed on the first display to a first user and the high quality video stream is displayed on the second display to a second user.

* * * * *